US007734423B2

(12) United States Patent
Crowley, Jr. et al.

(10) Patent No.: US 7,734,423 B2
(45) Date of Patent: Jun. 8, 2010

(54) METHOD, SYSTEM, AND APPARATUS FOR VIRTUAL MODELING OF BIOLOGICAL TISSUE WITH ADAPTIVE EMERGENT FUNCTIONALITY

(75) Inventors: William L. Crowley, Jr., Eagle, ID (US); Ullysses A. Eoff, Meridian, ID (US); Cap C. Petschulat, Boise, ID (US); Mason E. Vail, Nampa, ID (US); Richard D. Newman, Meridian, ID (US); Timothy L. Andersen, Boise, ID (US); Timothy Otter, Caldwell, ID (US); Robert W. Davis, Boise, ID (US)

(73) Assignee: Crowley Davis Research, Inc., Eagle, ID (US)

( * ) Notice: Subject to any disclaimer, the term of this patent is extended or adjusted under 35 U.S.C. 154(b) by 1231 days.

(21) Appl. No.: 11/234,413

(22) Filed: Sep. 23, 2005

(65) Prior Publication Data
US 2007/0233441 A1    Oct. 4, 2007

(51) Int. Cl.
*G06F 19/00* (2006.01)
*G01N 31/00* (2006.01)
*G06G 7/58* (2006.01)
(52) U.S. Cl. ............................... 702/19; 702/27; 703/11
(58) Field of Classification Search ................ None
See application file for complete search history.

(56) References Cited

U.S. PATENT DOCUMENTS

| | | | |
|---|---|---|---|
| 5,808,918 A | 9/1998 | Fink et al. | |
| 5,867,397 A | 2/1999 | Koza et al. | |
| 6,148,274 A | 11/2000 | Watanabe et al. | |
| 6,219,440 B1 | 4/2001 | Schaff et al. | |
| 6,360,191 B1 | 3/2002 | Koza et al. | |
| 6,505,180 B1 | 1/2003 | Crowley | |
| 6,556,961 B1 | 4/2003 | Lafe | |
| 6,701,236 B2 | 3/2004 | Ulyanov et al. | |
| 6,708,141 B1 | 3/2004 | Schaff et al. | |
| 2003/0018457 A1 | 1/2003 | Lett et al. | |
| 2006/0167637 A1 | 7/2006 | Agur et al. | |
| 2006/0251642 A1 | 11/2006 | Wolffe et al. | |
| 2006/0257928 A1 | 11/2006 | Zhang et al. | |
| 2009/0070087 A1 | 3/2009 | Newman et al. | |

OTHER PUBLICATIONS

Andersen, T., et al. (2005) A Biologically Derived Approach to Tissue Modeling, MMVR 13-Long Beach, CA, IOS Press, Amsterdam, J. Westwood et al., eds., Technology and Informatics 111:15-21.
Brenner, S. (1999) Theoretical Biology in the Third Milennium, Phil. Trans. Royal Society Lond. B 354: 1963-1965.
Chabanas, M., et al. (2003) Comparison of Linear and Non-Linear Soft Tissue Models with Post-Operative CT Scan in Maxillofacial Surgery, Laboratoire TIMAC-IMAG, CNRS UMR 5525, Universite Joseph Fourier-Grenoble Institut d'Ingenerie de l'Information de Sante, 38706 La Tronche cedex, France, et al. : 1.
Crossan, A., et al. (2000) Multi-Session VR Medical Training—The HOPS Simulator, Department of Computing Science, Faculty of Veterinary Medicine, University of Glasgow G12 8QQ, Glasgow, UK : 3.
Eggenberger, P. (1997) Evolving Morphologies of Simulated 3d Organisms Based on Differential Gene Expression, in P. Husbands et al., eds., Proceedings of the 4th European Conference on Artificial Life (ECAL97), Cambridge, Ma., MIT Press.
Eggenberger Hotz, P. (2003) Combining Developmental Processes and their Physics in an Artificial Evolutionary System to Evolve Shapes, in S. Kumar et al., eds., On Growth, Form and Computers, Amsterdam, Elsevier Academic Press: 302-318.
Elhelw, M.A., et al. (2004) Real-Time Photo-Realistic Rendering for Surgical Simulations with Graphics Hardware, Royal Society / Wolfson Medical Image Computing Laboratory, Imperial College London, London, UK : 2.
Forbes, N. (2004) Imitation of Life: How Biology is Inspiring Computing, Cambridge, Ma., MIT Press: 13-24.
Kirschner, M., et al. (1998) Evolvability, Proc. National Academy of Sciences USA, 95: 8420-8427.
Osada, R., et al. (2002) Shape Distributions, ACM Transactions on Graphics, 21:807-832.
Otter, T. (2004) Toward a New Theoretical Framework for Biology, GECCO 2004 Workshop on Self-Organization and Development (SOE):1-9.
Otter, T., et al. (2004) Gene and Body: Building and Maintaining the Phenotype of Living Organisms, 9th International Conference on the Simulation and Synthesis of Artificial Life, Workshop on Self-Organization and Development: 1-4.
Porto, V.W. (1997) Evolutionary Programming, Handbook of Evolutionary Computation, Release 97/1, IOP Publishing Ltd. and Oxford University Press: B1.4:1-10.
Sengers, B.G. (2005) Modeling the Development of Tissue Engineering Cartilege, Technische Universiteit Eindhoven, Netherlands : 5.
Stylopoulas, N., et al. (2002) CELTS: A Clinically-Based Computer Enhanced Laparoscopic Training System, The Simulation Group Massachusetts General Hospital-CIMIT, 65 Landsdowne Street, Cambridge, MA 02139 : 2-3, 6-7.
Sun, W., et al. (2002) Recent Development on Computer Aided Tissue Engineering—A Review, Computer Methods and Programs in Biomedicine 67:85-103.
Zhang, J., et al. (2003) Object Representation and Recognition in Shape Spaces, Pattern Recognition 36: 1143-1154.

(Continued)

*Primary Examiner*—Lori A Clow
(74) *Attorney, Agent, or Firm*—Lara J. Dueppen; Perkins Coie LLP

(57) ABSTRACT

A method system, and apparatus for virtual modeling of biological tissue yields virtual multicellular individuals that exhibit adaptive emergent functionality in response to environmental stimuli. Virtual environmental parameters and cells with genomes are generated, and modified by genetic operations. Cells are developed into generations of multicellular individuals, which are evaluated and selected via evolutionary search according to fitness criteria, and individuals exhibiting adaptive emergent functionality, such as self-repair, are developed and identified.

21 Claims, 20 Drawing Sheets

OTHER PUBLICATIONS

International Search Report, International Application No. PCT/US08/75514, Nov. 19, 2008, 2 pages.

Abbott, R., et al. (2006) "Simulating the Hallmarks of Cancer," *Artificial Life*, 12:617-634, 18 pages.

Andersen, T., et al. (2006) "Development of Virtual Embryos with Emergent Self-Repair," Technical Report FS-06-03, Proceedings of the AAAI Symposium on Developmental Systems (pp. 16-23), Arlington, VA, 8 pages.

Azevedo, R. B. R., et al. (2005) "The Simplicity of Metazoan Cell Lineages," *Nature*, 433:152-156, 5 pages.

Azevedo, R. B. R., et al. (2006) "Sexual Reproduction Selects for Robustness and Negative Epistatis in Artificial Gene Networks," *Nature*, 440:87-90, 4 pages.

Braun, V., et al. (2003) "ALES: Cell Lineage Analysis and Mapping of Developmental Events," Bioinformatics 19(7):851-858, 8 pages.

Di Ventura, B., et al. (2006) "From in vivo to in silico Biology and Back," *Nature*, 443(5):527-533, 7 pages.

E-Cell Project Steering Committee (Y. Naito, chair), (2008) "A Brief History of the E-Cell Project and the E-Cell System," Retrieved Feb. 2008, <http://www.e-cell.org/ecell/about/history>, 3 pages.

Eggenberger Hotz, P., (2005) "Asymetric Cell Division and its Integration with Other Developmental Processes for Artificial Evolutionary Systems," Artificial Life IX: Proceedings of the Ninth International Conference on the Simulation and Synthesis of Living Systems, J. Pollack, et al., eds., Cambridge, MA: MIT Press, 6 pages.

George, S., et al. (2003) "A Biological Programming Model for Self-Healing," Proceedings of the 2003 ACM Workshop on Survivable and Self-Regenerative Systems: in Association with 10th ACM Conference on Computer and Communications Security, pp. 72-81, 10 pages.

Grajdeanu, A., et al. (2006) "A Novel Developmental System for the Study of Evolutionary Design," Technical Report FS-06-03, Proceedings of the AAAI Symposium on Developmental Systems (pp. 24-30), Arlington, VA, 7 pages.

Grant, M., et al. (2006) "Stimulating Properties of an In Vitro Epithelial Cell Morphogenesis," *PLoS Computational Biology*, 2(10):1193-1209, 17 pages.

Hogeweg, P. (2000) "Evolving Mechanisms of Morphogenesis: on the Interplay Between Differential Adhesion and Cell Differentiation," *Journal of Theoretical Biology*, 203:317-333, 19 pages.

Izaguirre, J.A., et al. (2004) "CompuCell, a Multi-Model Framework for Simulation of Morphogenesis," *Bioinformatics*, 20(7):1129-1137, 9 pages.

Kajita, A., et al. (2002) "Physical Modeling of the Cellular Arrangement in C. elegans Early Embryo: Effect of Rounding and Stiffening of the Cells," *Genome Informatics*, 13:224-232, 9 pages.

Kumar, S. (2004) "Investigating Computational Models of Development for the Construction of Shape and Form," Dissertation, University of London, Department of Computer Science, 320 pages.

Kumar, S., et al. (2003) "Computational Embryology: Past, Present and Future," in Ghosh and Tsutsui, eds., *Advances in Evolutionary Computation: Theory and Applications* (pp. 461-478), New York, NY: Springer, 21 pages.

Nagpal, R., et al. (2003) "Programming Methodology for Biologically-Inspired Self-Assembling Systems," in Computational Synthesis: From Basic Building Blocks to High Level Functionality: Papers for the 2003 Spring Symposium, H. Lipson, et al., eds., Technical Report SS-03-02, pp. 173-180, American Association for Artificial Intelligence, Menlo Park, CA, 8 pages.

National Resource for Cell Analysis and Modeling (2006) "The Virtual Cell. VCell 4.3 Users Guide, Jun. 20, 2007," Retrieved Feb. 2008, <http://vcell.org/userdocs/Rel/user_guide.pdf>, 54 pages.

Platzer, U., et al. (2002) "Simulation of Genetic Networks in Multicellular Context," in Fifth German Workshop on Artificial Life: Abstracting and Synthesizing the Principles of Living Systems, D., Kim J. und Martinez T. Polani (eds.), pp. 43-51, Akad, Verl.-Ges, 10 pages.

Platzer, U., (2003) "Simulation of Genetic Networks in Multicellular Organisms," Ph.D. Dissertation, Naturwissenschaftlich-Mathematische Gesamtfakulat der Ruprecht-Karls-Universitat, Heidelber, Germany, 112 pages.

Platzer, U., et al. (2004) "Genetic Networks in the Early Development of *Caenorhabditis elegans*," International Review of Cytology, 234:47-100, 28 pages.

Smallwood, R., et al. (2006) "The Epitheliome Project: Multiscale Agent-based Modeling of Epithelial Cells," 34d IEEE International Symposium on Biomedical Imaging: Nano to Micro, 6(9):816-819, 4 pages.

Stanley, K. O., et al. (2003) "A Taxonomy for Artificial Embryogeny," *Artificial Life*, 9:93-130, 39 pages.

Tomita, M., et al. (1999) "E-CELL: Software Environment for Whole-Cell Simulation," *Bioinformatics*, 15(1):72-84, 13 pages.

Tomlin, C. J., et al. (2007) "Biology by Numbers: Mathematical Modeling in Developmental Biology," *Nature Reviews: Genetics*, 8:331-340, 10 pages.

Wanner, B. L., et al. (2005) "Modeling the *E. coli* Cell: The Need for Computing, Cooperation, and Consortia," in *Systems Biology*, L. Alberghina and H.V. Westerhoff, eds., Springer-Verlag, Berlin, pp. 163-189, 27 pages.

Fig. 1

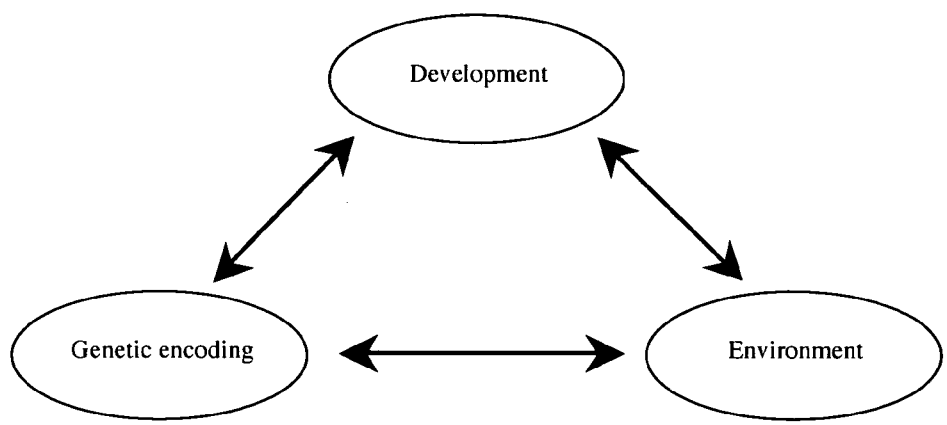

The essential biologically derived features of our ontogeny engine include genetic encoding, a process of self-construction analogous to biological development, and an environment that guides the processes by which the organism is so constructed. Although these features are depicted as independent domains, the arrows indicate that they are in fact interdependent, overlapping components.

An integrated model for ontogeny.
Arrows: E, gene expression; M, Metabolism; C, cell signaling; S, sensory processes; R, gene regulation.

Emergent Functions of the Multicellular State
*(Manifestations of order)*

Differentiation    (specialization)
Communication    (sensory functions, exchange)
Homeostasis    (regulatory processes, feedback)
Metabolism    (fuels, energy, synthesis)
Self-repair    (turnover, regeneration, replication)
Adaptation    (phenotypic plasticity)

The Evolutionary Search Space

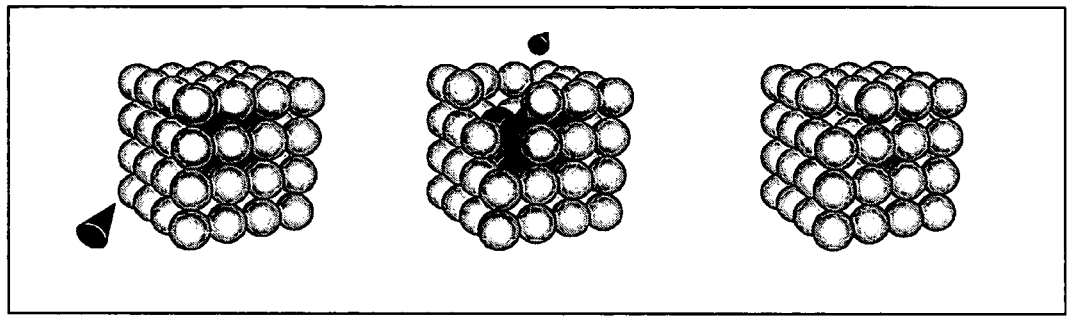

Cube embryo; fitness 1.0 individual produced by a GA search. Self-repair of the cube after being damaged by a projectile (conical shape, 1st panel, lower left). The projectile approaches the cube from the lower left, passing upward, through, and exiting near the midpoint of the upper surface, leaving a visible hole (middle image). Dark inner cells are ready to divide. A partially repaired embryo (right image), still missing a cell along the left front edge.

Figure 9

Growth stages of a 5 x 5 x 1 sheet embryo. Number pairs indicate [time step when this image occurred] / [# cells present]. Thus, the 1$^{st}$ image with 13 cells was captured at the 19$^{th}$ time step.

Gene network for the sheet embryo; genes: G1, G2,... molecules: $M_A$, $M_B$; receivers: R1, R2; senders: S1,S2. ▶ stimulatory effect; ■ inhibitory effect; ○ substance produced. Molecules $M_A$ and $M_B$ also have inhibitory connections to genes 3 through 16, but for clarity only 4 connections are shown.

System Architecture

Self-Repair of a Hollow Sphere

METHOD, SYSTEM, AND APPARATUS FOR VIRTUAL MODELING OF BIOLOGICAL TISSUE WITH ADAPTIVE EMERGENT FUNCTIONALITY

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Contract DAMD17-02-2-0049 as awarded by the US Army Medical Research Acquisition Activity (USAMRAA).

CROSS REFERENCES TO RELATED APPLICATIONS

None.

TECHNICAL FIELD OF THE INVENTION

This invention is in the technical field of means or steps for modeling or simulation of biological cells or tissues.

BACKGROUND OF THE INVENTION

Attempts have been made to model virtual biological tissues exhibiting adequate fidelity with living tissue. [Stylapaulas, N., Cotin, S., Dawson, S., Ottensmeyer, M., Neumann, P., Bardsley, R., Russell, M., Jackson, P., Rattner, D. (2002) CELTS: A Clinically-Based Computer Enhanced Laparoscopic Training System, The Simulation Group Massachusetts General Hospital-CIMIT, 65 Landsdowne Street, Cambridge, Mass. 02139: 2-3, 6-7; Crossman, A., Brewster, S., Reid, S., Mellor, D. (2000) Multi-Session VR Medical Training—The HOPS Simulator, Department of Computing Science, Faculty of Veterinary Medicine, University of Glasgow G12 8QQ, Glasgow, UK: 3; Chabanas, M., Payan, Y., Marecaux, C., Swider, P., Boutault, F. (2003) Comparison of Linear and Non-Linear Soft Tissue Models with Post-Operative CT Scan in Maxillofacial Surgery, Laboratoire TIMC-IMAG, CNRS UMR 5525, Université Joseph Fourier—Grenoble Institut d'Ingénierie de l'Information de Santé (In3S), 38706 La Tronche cedex, France Service de chirurgie maxillo-faciale et plastique de la face, Hôpital Purpan Toulouse Place Baylac BP 3103, 31059 Toulouse Cedex 3, France Laboratoire de Biomécanique, EA 3697, Université P. Sabatier, Hôpital Purpan Amphithéâtre Laporte, Place Baylac BP 3103-31059 Toulouse cedex 3, France: 1; Sengers, B. G. (2005) Modeling the development of tissue engineered cartilage, Technische Universiteit Eindhoven, Eindhoven, Nev.: 5; ElHelw, M. A., Lo, B. P., Darzi, A., Yang, G. (2004) Real-Time Photo-Realistic Rendering for Surgical Simulations with Graphics Hardware, Royal Society/Wolfson Medical Image Computing Laboratory, Imperial College London, London, United Kingdom: 2] Lack of adequate fidelity hinders medical and biological research, simulation, and practice. Lack of fidelity is realized in two distinct ways:

- poor or limited simulation of tissue response to or recovery from external stimuli (e.g., surgery, drug treatment), and
- poor or limited simulation of tissue development and internal processes (e.g., metabolism, homeostasis, aging, disease).

Further, current models and their computational engines lack a comprehensive and biologically realistic basis and instead rely on incomplete, static, or otherwise inadequate assumptions that do not encompass the range or complexity of biological relationships necessary to properly generate the models. Specifically, lack of such support in current genetic algorithm (GA), evolutionary computing (EC), and biologically inspired computing (BIC) techniques and practices provides an opportunity for improving both the art of biological tissue modeling and the state of computer science and technology.

Tissue Modeling Fidelity:

Most models of biological tissues are based on principles of systems engineering [Sun and Lal, 2004]. For example, tissue structure and elasticity can be modeled as dampened springs, electrically excitable tissues as core conductors, and tissues such as blood according to principles of fluid mechanics. As different as these models are, they share a number of general features: they are constructed from the perspective of an external observer and designer of the system; they are grounded in laws (Hook, Kirchoff, Ohm, Bernoulli, etc.) that describe predictable behavior of the physical world in a manner that can be verified empirically, by measurement; they incorporate feedback controls to optimize system performance by tuning of adjustable elements; their complexity requires some kind of computational approach.

Although models based on a systems engineering approach contain a few features that mimic the way that natural living systems are built and how they function, such models fail to capture important emergent properties of natural systems.

Current tissue models are based on a deterministic, top-down approach, whereby all features must be incorporated into a pre-specified plan conceived and constructed by an intelligent designer. Top-down tissue models are based on analysis of static or time-averaged images using zoom focus, viewing an object with increasingly fine resolution where the locations of certain attributes or properties are plotted at specific locations on a map of the object of interest. They emphasize the anatomy of the organ as it exists, but they fail to capture where the organ came from and how it developed. Top-down modeling is appropriate for designing buildings, machines, or other objects of human engineering wherein form and function are imposed by external agents. However, living organisms are not machines and so top-down approaches fail to capture and leverage essential emergent functions of self-organizing systems such as self-construction via development (ontogeny), self-repair, metabolism, homeostasis, and adaptability (the ability to monitor and respond to complex, unpredictable environments).

TABLE A

General features of natural systems compared to human-designed systems

| | Natural Systems | Human-engineered Systems |
|---|---|---|
| Design | Selection by evolutionary process | Optimization by architect |
| Construction | Self-constructs by development; continuous turnover of components | Built by a separate process and apparatus prior to operation |
| Control | Feedback, homeostasis, self-repair, regeneration | Automated feedback |
| Tuning/ Operation | Contingent, adaptable and plastic; monitors complex, unpredictable environment | Task-specific; monitors only a few parameters |

Evolutionary Computing and Biologically Inspired Computing:

Existing computational models for virtual representation of biological designs rely on relatively simplistic, not fully accurate, or narrow perspectives about living organisms and the processes by which they are constructed. Existing models appear to incorporate genes, genotype, phenotype, emergence, self-repair, and other biologically derived features, but upon closer inspection definitions of these terms have been broadened or changed so that their meaning and relevance to living systems is lowered [Forbes, 2004; Otter and Davis, 2004]. For example, the "crossover" mechanism used in evolutionary computation to effect reshuffling of genes between individuals bears little resemblance to any biological process: crossover conflates three different biological processes, namely, random segregation of chromosomes during meiosis, random fertilization, and a phenomenon that biologists call "crossing over" which takes place within a single individual [Hartwell et al., 2004]. Thus, the term "crossover" has been assimilated without the underlying complexity and richness of biological mechanisms [Back et al., 1997].

Deficiencies in terminology are particularly noticeable regarding the cellular basis of development, which is the primary domain of biology that supports the present invention. A few examples are outlined below.

Genotype→Phenotype Mapping

A fundamental shortcoming of conventional GA approaches is simplistic modeling of the relationship between phenotype and genotype. Problems with genotype-phenotype mapping can be traced to two main sources:

1. Inconsistent and broad usage of the term 'gene', and its derivatives (genetic);
2. Inadequate models for extrapolating from a single gene and what it encodes to a complete set of genes and what they specify collectively.

In evolutionary computation the term "gene" refers to a broad range of objects, including: simple bit strings where each position is equivalent; coded representations of phenotypic characters; representations of characters that are subject to control, as individual genes or in groups; genes that encode either phenotypic characters or agents that control the activity of other genes. These are not equivalent meanings, yet they are grouped under the heading of genetic encodings.

The above definitions are based on simple, direct mapping of genotype onto phenotype, a corollary to the dogma that genotype defines the phenotype. The central dogma outlines the steps involved in expression of a single gene, but this simple 1:1 mapping does not explain the global relationship between genotype and phenotype. As recent cloning experiments confirm [Shin et al., 2002], genotype is not adequate to specify phenotype. Genotype does not specify when or where genes are transcribed, how proteins assemble into macromolecules, signaling or metabolic networks, nor any other aspect of cellular function on a higher level of organization. In modeling, a simple gene-based perspective is not adequate because it fails to capture the interaction of gene products, control of gene expression, cell signaling, epigenetic processes, and other complexities of biological systems.

Developmental Paradigms

Biological development is the process that best captures the power of biology. During human development a single cell, the fertilized egg, is transformed over a period of 38 weeks into a complex, integrated creature containing ~10 trillion ($10^{13}$) cells, as the simple instructions encoded in the egg and sperm produce a fully formed, if miniature, human being [Boal, 2002]. This description highlights two aspects, the potential of scale, and the potential of building complexity from simplicity. As seductive as this view may be, taken literally it is misleading and untrue, because it suggests that all of the complexity of a human being is bound up in its genetic code.

During development the embryo is constructing itself, and part of this process involves shaping an environment suitable for development and monitoring it. Genes determine the types of sensors a cell can make, but once a cell builds and deploys sensors, it begins to collect information that is not genetically encoded. Living organisms produce, detect, and record such signals and recognize patterns that are crucial to survival and reproduction. The complex relationships among genetically encoded components, development, and phenotypic plasticity of living organisms are not captured in current models, primarily because the models have been designed from a gene-centered perspective.

A living body, once constructed, remains in a dynamic, continual state of renewal and repair, in spite of its deceptively static appearance [Harris, 1987]. As old parts wear out or become damaged, they must be replaced. This implies that there is a turnover of materials and even more, mechanisms for checking the condition of parts (damage or error detection/proofreading), mechanisms to remove the damaged ones, and mechanisms to replace them. Current tissue models do not include these functions.

While in a sense biological development is the process of constructing an organism, construction usually is directed by an intelligent agent, whereby shape is imposed. Using this convention, top-down models appear more like buildings or perhaps blueprints of buildings than they do living organisms. Yet living systems are capable of self-construction using available resources, and the continuous recycling and replacement of old, worn, or damaged components produces "anatomical homeostasis" [Harris, 1987]. Accordingly, a living organism is more a fountain than a statue: both have definite form, but the fountain's form is incidental to the flow of materials though it, and in the statue, form is primary and static. Current models rely on form to map function. A failure to recognize the inadequacy of the statue metaphor impedes the ability to construct appropriate models of living organisms. A living body remains in a dynamic state, and so too, should virtual tissues generated by modeling.

Living organisms are remarkably resilient, fault tolerant, and during development, convergent on a desirable outcome, healthy offspring. In contrast, systems such as L-systems (grammar based), Turing Machines, and Cellular Automata (CAs) are typically not fault tolerant or robust in function. These systems are brittle in the sense that a slight perturbation in either initial conditions or in the rules of the system often leads to drastic changes in final outcome. Current computational systems lack fault tolerance because they are based on prescribed functions rather than processes that derive from interaction of versatile components.

The present invention represents an improvement over prior disclosures primarily from the perspective of higher ordered emergent functionality having been achieved. For example, it is submitted that the term "emerge" and its derivatives as used in U.S. Pat. No. 6,360,191 refers principally to the fact that a suitable solution to a design problem was found ("emerged" as stated in the patent) through an evolutionary search process. By contrast, the present invention has achieved truly adaptive emergent functionality in the forms of cell signaling, feedback, repair and even oscillatory behavior in accordance with biological fidelity.

Additionally, the disclosures of U.S. Pat. No. 6,360,191 and U.S. Pat. No. 5,867,397, referenced therein, imply that there is a limited and direct correspondence between genotype and phenotype, whereas the instant invention improves the representation of environmental factors and the delicate balance that exists as feedback between genome, environment and phenotype as manifest in gene expression, metabolism, cell signaling, sensory processes and gene regulation that actually form the basis for the present invention's premise, and upon which substantial genetic and biological evidence exists.

While the relatively straight-forward process of chromosomal-like splicing and resulting sexual "crossover" of U.S. Pat. No. 6,360,191 fit the genetic programming (referred to therein as a hierarchical genetic algorithm) process, the instant invention is submitted to improve the level of reference to the broader effect of environmental factors providing a more complete and descriptive genetic operation, with a broader approach as compared to the prior disclosures' narrower field of complex structural design achieved through a simulated natural selection process.

As in the above discussion of U.S. Pat. No. 6,360,191, the present invention is contrasted with U.S. Pat. No. 6,148,274 primarily from the perspective that the instant invention is seen to provide improvement in that adaptive emergent functionality was achieved. Also, as compared to the disclosure thereof, the instant invention provides a more logically faithful process by which the present invention carries out its evolutionary search function. In contrast, the disclosure of the referenced patent obtains solution vectors such as those deduced from user preferences and through the use of optimization adjustment techniques, the methods therein disclosed aspire to enhance local solution search abilities within the conventional genetic algorithm framework.

Furthermore, the referenced disclosure of U.S. Pat. No. 6,148,274 deals principally with the view that biological evolution occurs solely within a sexual "crossover" context, which is not accepted as a supported premise in the model of the instant invention.

The present invention is distinct from U.S. Pat. No. 6,701,231 based on its stated field of application, namely the optimization of control systems as well as its fundamental approach toward solving that class of problems. Specifically, the referenced patent attempts to solve a class of feedback processes through the deployment of a neural network that is trained by a genetic analyzer. The instant invention also is distinct over the disclosure in the improved fidelity of its model to the biological principles and related phenomena in question. The cited disclosure does not solve the problem of developing emergent behavior or provide a bottom-up approach to problem solving as in the instant invention.

The present invention is distinguished from U.S. Pat. No. 5,808,918 primarily on the basis that the patent's disclosure deals with abstractions of collected data structures at presumed and various levels of scale. The process described therein deals more with a systems engineering approach to simulation and is submitted to be top down and reductionist in nature, in contrast to the present invention's method of utilizing biological primitives in conjunction with the ontogeny engine in the example embodiment and an advanced evolutionary search method to achieve biologically accurate and adaptive emergent functionalities in the form of derived virtual tissue. Additionally, the disclosure of the patent does not provide for emergent functionality, behavior or properties, features, which comprise a fundamental principle of biological development and are an object of the present invention.

The present invention differs from U.S. Pat. No. 6,556,961 in several ways. The most significant is the field of application, namely the systems engineering approach to solving differential equations as a modeling concept and as incorporated within a cellular automata framework. Aside from the lack of any feature within the referenced patent which would support a truly emergent property or function, the sheer reliance on partial differential equations as the backbone for a proposed solution space to the class of problems which the present invention addresses is in a different context altogether. Since the thrust of the referenced patent is a somewhat automated solution for partial differential equations couched in a cellular automata environment, the prospect of achieving truly emergent functionalities, properties or behavior by the referenced patent and as required and demonstrated by the present invention is remote.

TABLE B

Contrast of Evolutionary Search Characteristics To Present Invention

| Characteristic | Conventional Genetic Algorithm | Improved Model For Evolutionary Search In the Present Invention |
| --- | --- | --- |
| Population Size | Large (typically 250 to 10,000+) | Small (5 to 250) |
| Mutation Rate | Very Low (typically 0.001% to 1.000%) | Very Large (1.0% to 50%+) |
| Recombination | Sexual "Crossover" At Every Generation | Rare or no sexual "crossover" |
| Environment | Fixed or undefined | Mutable and searchable |
| Adaptive Emergent Functionality | None | Demonstrated With Continual Development and Repair |

The present invention exploits this advanced evolutionary search model to bring an improved result in a realistic and effective approach for virtual tissue modeling.

SUMMARY OF THE INVENTION

To solve these and other problems, the present invention provides a method, system, and apparatus to devise tissue models that conform more closely to the living systems they emulate, by incorporating biologically-derived primitives into a computational framework. The invention is based on the paradigm of biological development, focusing on cells, cellular processes, and the multicellular body plan.

The most fundamental compartment of living systems is the cell, the smallest unit capable of self-replication. Accordingly, the invention focuses on simulations of cellular function: each cell contains a genome, and processes such as division, differentiation, growth, and death are encoded in gene-like data structures, without reference to their complex biochemical basis in vivo. The invention includes a developmental engine that carries out transformation of a single virtual cell into a multicellular virtual embryo, and it includes genetic operators that mutate, duplicate, or recombine genes.

TABLE C

Biological Primitives and Their Representation in Ontogeny Engine

| Biological Primitive | Representation in Invention's Computational Platform |
|---|---|
| Compartments | Cells, each with genome containing gene-like elements |
| Self-replication & Repair Adaptation | Cell division and growth; replacement of dead cells Evolutionary search engine with genetic operators, including multiple mutation operators, and defined fitness function |
| Selective Communication | Signals to/from environment and neighboring cells; gene regulatory networks |
| Energy Requirement | Growth substance ≧ threshold value |

The present invention incorporates a bottom-up approach to modeling. It models virtual tissues by a process that faithfully captures many features of biological development in algorithmic forms, and integrates them in an ontologically realistic framework. The premise is to focus on primitives by shifting the architect's role from designing final solutions to designing versatile components that may contribute to solutions that the architect could not likely anticipate. In other words, the architect's role is to enable, not specify. Solutions are then devised by an automated process of searching through populations of candidate solutions that are subject to mutation or recombination. The available primitives must provide versatility, range of function, and capacity for fine tuning that are sufficient to enable emergent functionality to arise from their interactions.

For example, the inventors have designed a genome that:
 is an assemblage of several types of genes, each with distinct encoding and control regions and a correspondingly diverse array of mutation operators, well beyond the limited scope of traditional evolutionary algorithms, and
 operates in a rule-based architecture using biological processes such as cell division, cell death, cell signaling, and control of gene expression.

The invention has been applied to the problem of automatic encoding of a digital genome that develops into a virtual tissue, with emergent capacity to repair itself when damaged. A 64-cell cube-shaped block and other tissue shapes, such as sheets and hollow spheres of cells, also with the capacity for self-repair, have been developed utilizing the invention. Capacity for self-repair is an emergent functionality derived from, but not specified by, the rule sets and primitives used to generate these virtual tissues. Tissue phenotype results from interaction of genetically encoded elements with the environment defined by the engine, and improvements in phenotype arise through an iterative evolutionary process guided by the described evolutionary search strategy.

The ability to repair damage or injury is an emergent property of tissues evolved by the computational engine of the present invention. Capability for self-repair is not specifically encoded in any gene or specified by any rule, nor is this capability a factor in calculating the fitness during the evolutionary search, but rather, capacity for self-repair arises from biological primitives (e.g., signaling between cells, gene networks, feedback mechanisms, etc.). None of these biological primitives explicitly encodes the ability to repair damage, but when taken together they tend to make the process of construction robust to large disruptions. For example, a cube model produced by an example embodiment herein recovers from damage sustained during development and even after 63 of its cells are destroyed, the 64-cell cube can regenerate itself perfectly from a single core cell.

This invention provides an automated, bottom-up approach to tissue modeling, the goal of which is to derive higher-level properties of biological systems—self-construction, self-repair, feedback, resilience to perturbation, and adaptability—from low-level biological primitives, allowing the system to evolve these primitives to an appropriate state and combination capable of achieving a desired target. This differs significantly from standard, top-down tissue modeling, where any higher-level biological properties must be explicitly designed and incorporated into the system.

In the detailed description herein of a method, system and apparatus for virtual modeling or simulation of biological cells or tissues, specific details are provided to offer full understanding of the invention, but it will be apparent to one skilled in the art that the invention may be practiced without such particulars. Descriptions herein utilizing literal language indicating actual physical processes at times are representative not of actual physical manipulation, but of operations on data within computers, as is common in the relevant art. The invention is not described with reference to any particular computer equipment, program, programming language, or equipment, and the method and system can, as will be appreciated by anyone skilled in the art, be executed utilizing any suitable apparatus.

BRIEF DESCRIPTION OF THE DRAWINGS

FIG. 1 is a diagram schematically illustrating an Ontogeny Engine Overview.

FIG. 9 is an illustration of Self Repair of the Cube After Injury.

DETAILED DESCRIPTION OF THE INVENTION

Figure 2:
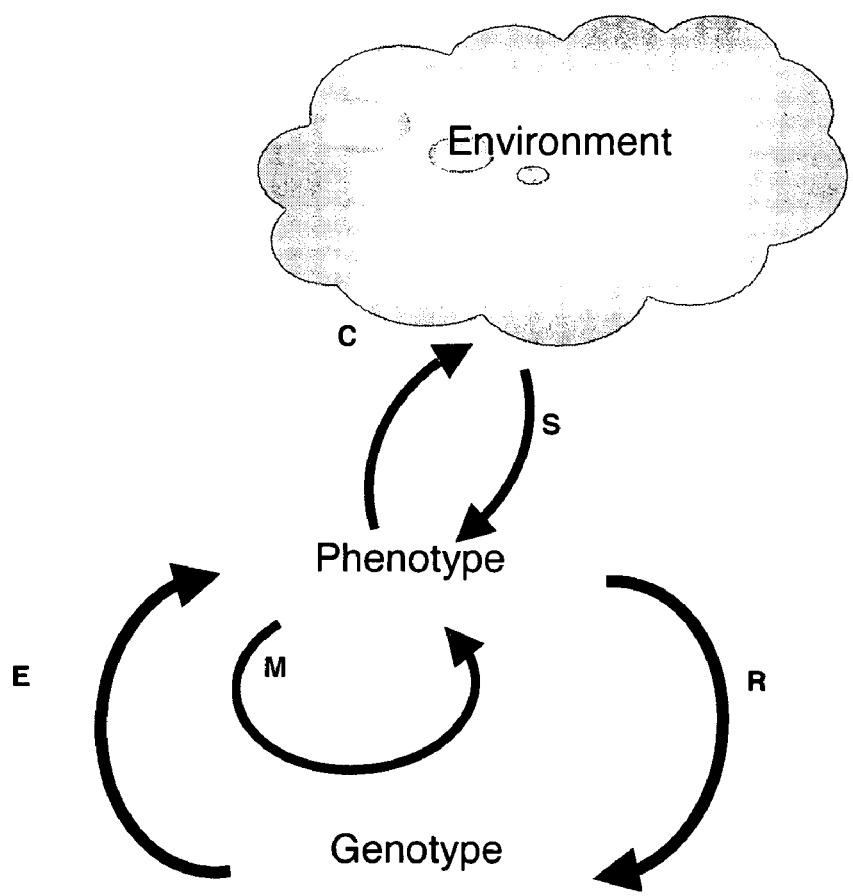
FIG. 2 is a diagram schematically illustrating the Overview of the Integrated Model for Ontogeny.

The conceptual framework for the present invention derives from avoiding the misleading and limiting perspectives suffered by previous art, specifically shifting from a gene-based model of phenotype to a cell-based perspective. Together with more comprehensive and faithful implementation of biological principles, the cell-based approach to modeling of this invention results in novel features that have been difficult, if not impossible, to achieve by conventional approaches.

Conceptual Basis for the Present Invention

The method, system, and apparatus of this invention include a computational approach and platform that incorporates principles of biology, particularly those primitive features of living systems that are fundamental to their construction and operation and that distinguish them from non-living systems. The goal in doing so is to identify, extract, and capture in algorithmic[1] form the essential logic by which a developing system self-organizes and self-constructs. The strategy involves shifting perspective to one that is based on the properties of cells, embedded within the developing system.

[1] List of biological primitives, implemented or planned: genome; membrane; extracellular matrix (ECM); divide; grow (get bigger); move/migrate; maintain a particular shape; change shape; specialize (differentiate); send & receive signals; age & die; memory of recent conditions/state/signals; become polarized (top/bottom/sides); adhesion/connection of other cells (physical and/or chemical); contract (shorten and/or exert force); become receptive (enter a "pre"-state).

The core concept for the invention is biological development, or ontogeny, the process by which a multicellular body is constructed, starting with a single cell, the fertilized egg. Ontogeny is the process by which one cell becomes a many-celled organism, and so the computational model focuses on the cellular primitives that are necessary to produce an integrated multicellular state: e.g., differentiation (specialization) of cell clusters, communication and feedback between specialized clusters, and metabolism to supply energy required to sustain such an organized state.

Specifically the main features of the developmental engine are 1. one cell→many cells by processes of cell division and/or death of cells
2. each cell is descended from another parent cell, so development includes lineage and sequential order
3. a modular body plan where each cell is a semi-autonomous unit with its own set of genes
4. Context-dependent, cell-by-cell control of gene expression via signaling.
5. construction and monitoring of the extra cellular environment
6. higher order (emergent) properties such as self-repair The computational engine used in the method, system and apparatus of this invention models tissue phenotype (appearance, traits, properties) as the result of a developmental process starting from a single cell and its genome. Properties such as tissue shape and self-repair arise from the interaction of gene-like elements as the multi-cellular virtual tissue develops. The engine defines and controls all parameters of the virtual environment necessary for development, including placement of nutrients, defining space for cells to grow, sequencing of actions, and rules that govern the physics of the virtual environment. To make the model more flexible, all of the environmental parameters (e.g., rules governing the calculation of molecular affinity and the placement and concentration of nutrients or other molecules) are configurable at run-time.

The ontogeny engine includes three main components: genetic encodings, a developmental process, and an environment in which development takes place, as illustrated in FIG. 1. The essential biologically derived features of the ontogeny engine include genetic encoding, a process of self-construction analogous to biological development, and an environment that guides the processes by which the organism is so constructed. Although these are listed as three distinct elements, in fact they are linked in complex, intricate ways. In principle, any of these components can be adjusted to devise a solution to a given problem.

Layered on top of ontogeny is a criterion of suitability, a basis for evaluating the outcomes of many schemes for development-different genetic encodings, different methods of construction, or different environments. This latter component, analogous to evolutionary processes of selection and descent with modification from ancestral forms, is represented in the computational architecture as a search process and a fitness function by which each individual solution is measured, and subsequently culled or retained, and possibly modified, for future generations. Evaluation and selection by a fitness criterion establishes a basis for competition among the members of a population of solutions, and a strategy for iterative improvements whereby the most successful solutions of one generation contribute more to the next generation.

Genes are an essential part of the computational design. Genes provide an important resource for the developing embryo: each cell contains a genome, a set of templates for producing proteins and other molecules needed to build and coordinate the multicellular aggregate. For genes to function as units of development, there must be a means to control how, where and when particular genes are expressed. To represent these features faithfully in the computational model of this invention, each virtual gene contains both regulatory and structural regions, and gene activity is controlled by the interaction of molecules ("transcription factors") with the regulatory region, in a parallel manner with gene regulatory networks in vivo.

Genes account for a good deal of the biological potential of scale whereby complexity arises from a relatively simple set of encodings. Yet for this potential to be realized, genetic information must be rendered by a process of self-construction, by development. Self-construction by living systems is driven (literally, by energy flux) in a manner that harnesses the power of genetic encodings to ensure heritability of traits, while packaging them in an encoded form that is compact enough to place into a single cell, the smallest living unit.

In FIG. 2, a diagram showing an overview of the integrated model for ontogeny, is shown relationship between gene expression, metabolism, cell signaling, sensory processes and gene regulation. As schematically illustrated in FIG. 2, integration of genes into the context of development requires that each gene's encoded product be understood in the manner that it contributes to cellular function or its coordination in the growing multicellular embryo (FIG. 2). For instance, some genes encode sensor molecules that allow cells to detect signals from neighboring cells. However, while genes determine the types of sensors a cell can make, genes do not specify the patterns of information that the cell receives. Accordingly, phenotype represents a higher ontological category than genotype, since the phenotype has access to genetically encoded information and information in its environment that is not so encoded. Furthermore, cells control which genes are expressed and so the patterns of gene expression across the entire embryo derive from controls each cell applies according to the signals it receives. Signals are locally defined, by the position a cell occupies in gradients in the developmental field, and by the signal molecules produced by the cell's neighbors. Microenvironments and control of gene expression are the basis for differentiation. In addition to their role in development, genes serve a passive role as units of inheritance, the units for transfer of information across generations For genes to serve as units of inheritance they must have a stable, but not completely unchangeable, structure and changes that occur in the structure of genes must be able to be passed on to progeny. Genetic variation is the basis for novelty, both in the present invention and in vivo, and so each generation of solutions is subject to genetic operators (mutation, duplication, deletion, or recombination carried out by the evolutionary engine) before another round of development takes place.

Emergence is of fundamental importance to the current invention. Emergence is a term that carries many special meanings, and accordingly, a broad range of phenomena have been classified as emergent [Steels, 1994; Morowitz, 2002]. With regard to this invention, emergence refers to a special relationship among primitives or agents in a multi-agent system. Only a specific arrangement or interaction among primitives produces the emergent behavior, and such behavior is not a property of any single primitive. Usually, emergence refers to behaviors or dynamic states rather than static shapes or structures. In living systems, emergence carries one or more additional meanings: 1) that the property of interest appears only at some higher level of hierarchical organization than the elements that give rise to it; 2) that the emergent behavior is adaptive, that it carries survival value, or increases fitness. For instance, homeostasis among vertebrates (maintenance of blood composition within narrow limits) satisfies both conditions. It is adaptive, and it is a whole organism property that involves organs in several different body systems (primarily kidneys, heart, brain, and in some animals, skin or salt glands).

Figure 3:
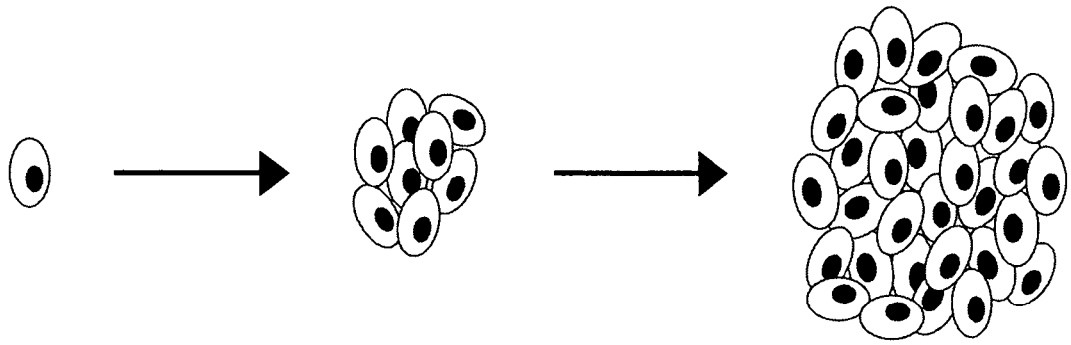
FIG. 3 is a diagram schematically illustrating Emergent Functions of the Multicellular State.

FIG. 3 is a diagram showing emergent adaptive functionalities manifested as differentiation (specialization), communication (sensory functions, exchange), homeostasis (regulatory processes, feedback), metabolism (fuels, energy, synthesis), self-repair (turnover, regeneration, replication) and adaptation (phenotypic plasticity). As schematically illustrated in FIG. 3, the emergent functionalities of interest for the present invention concern those properties that have survival value for embryos because they serve needs of the multicellular state produced by ontogeny (FIG. 3). Embodiments of the present invention have demonstrated its utility for producing emergent self-repair, cell communication that leads to the desired form, and a feedback network that produces regular oscillations of state that propagate through the embryo.

After the parameters of the virtual environment are configured, development is initiated by placing a single virtual cell having a genome into that environment. The cell's genome then interacts with any molecules in the environment as well as any molecules that are produced internally by the cell. Depending upon these interactions, each gene within the cell may be turned on (or off). When a gene is turned on, the transcription apparatus of the cell produces the molecules defined by the gene's structural region. These newly produced molecules may in turn interact with the cell's genome, affecting rates of transcription at the next time step. Development is thus governed by inputs from the virtual environment external to the cell, and also by internal feedback mechanisms of the cell.

In addition to transcription, two primary actions—cell death (apoptosis) and cell growth/division—are available to each cell. The genome of a cell may include genes that encode death molecules (and/or growth molecules), and as these genes are transcribed, the concentration of encoded molecules in the cell's cytoplasm increases. Growth or death is then a function of the concentration of these two types of molecules. When a cell dies, it is removed from the environment. Alternately, if a cell grows and divides, a new cell is placed in a location adjacent to the parent cell. If all adjacent positions are already occupied, that cell may not divide, even if the concentration of growth substance exceeds the threshold for growth.

In addition to environmental factors and internally produced molecules, a cell may also receive information from neighboring cells. The simplest neighborhood of a cell consists of those cells that are spatially adjacent to (touching) the cell of interest. However, a cell's neighborhood may be configured as any arbitrary group of cells. For example, a neighborhood (the cells to/from which it will send/receive signals) could include cells that are not adjacent, as occurs in vivo with cells that are able to signal non-local cells via hormones.

Cellular signaling is based on a handshake approach that requires both the sender and the receiver to create specific molecules for a signal to be transmitted. To send a signal, a cell must create molecules of type 'signal'. At each time step, each cell determines which cells are in its neighborhood and presents the signal(s) it has produced to its neighbors. For a cell to receive a signal that is being presented to it, the cell must build receiver molecules that are tuned to the signal. This completes the handshake portion of the cell signaling process—i.e., for a signal to be passed between two cells, the signal sent must be compatible with the receiver molecules built by the receiver cell. Finally, when a receiver senses a signal for which it is designed, it generates an internal signal that is defined by the receiver molecule (which is ultimately defined and produced by the cell's genome), but is independent of the particular signal a receiver molecule is designed to detect. This third component has been decoupled from the receiver and signal to allow different cells to produce entirely different internal signals from the same external stimulus. The strength of the internal signal is a configurable function of the concentration of signal molecules produced by the sender and the concentration of receiver molecules that the receiver has produced.

To automate the process of tissue modeling, an evolutionary search process is used to search for a genome with the proper encoding to render the desired (target) tissue shape and function. Typically a seed population of cells, each with a different genome, develops to yield a population of individuals, each a multicellular tissue with different properties. An individual is defined by both its genome and the configuration that develops it; during evolution this permits modification of the genome (using genetic operators) or alteration of the context for development, or both.

Three basic steps are required to process each individual in the population. First, an environment is instantiated using the configuration specified by that individual, and a single cell with a defined genome is placed in that environment. Then the ontogeny engine is allowed to run until a stable configuration is reached (or a maximum number of time steps are reached).

After each individual in a population has been evaluated and scored according to a fitness function, the GA selects a subpopulation, usually those individuals with the highest fitness, as the starting set for the next generation. Genetic operators (mutation, duplication, deletion, or cross-over) increase the genetic variation of the seed population for another round of development, and the cycle repeats.

Figure 4:
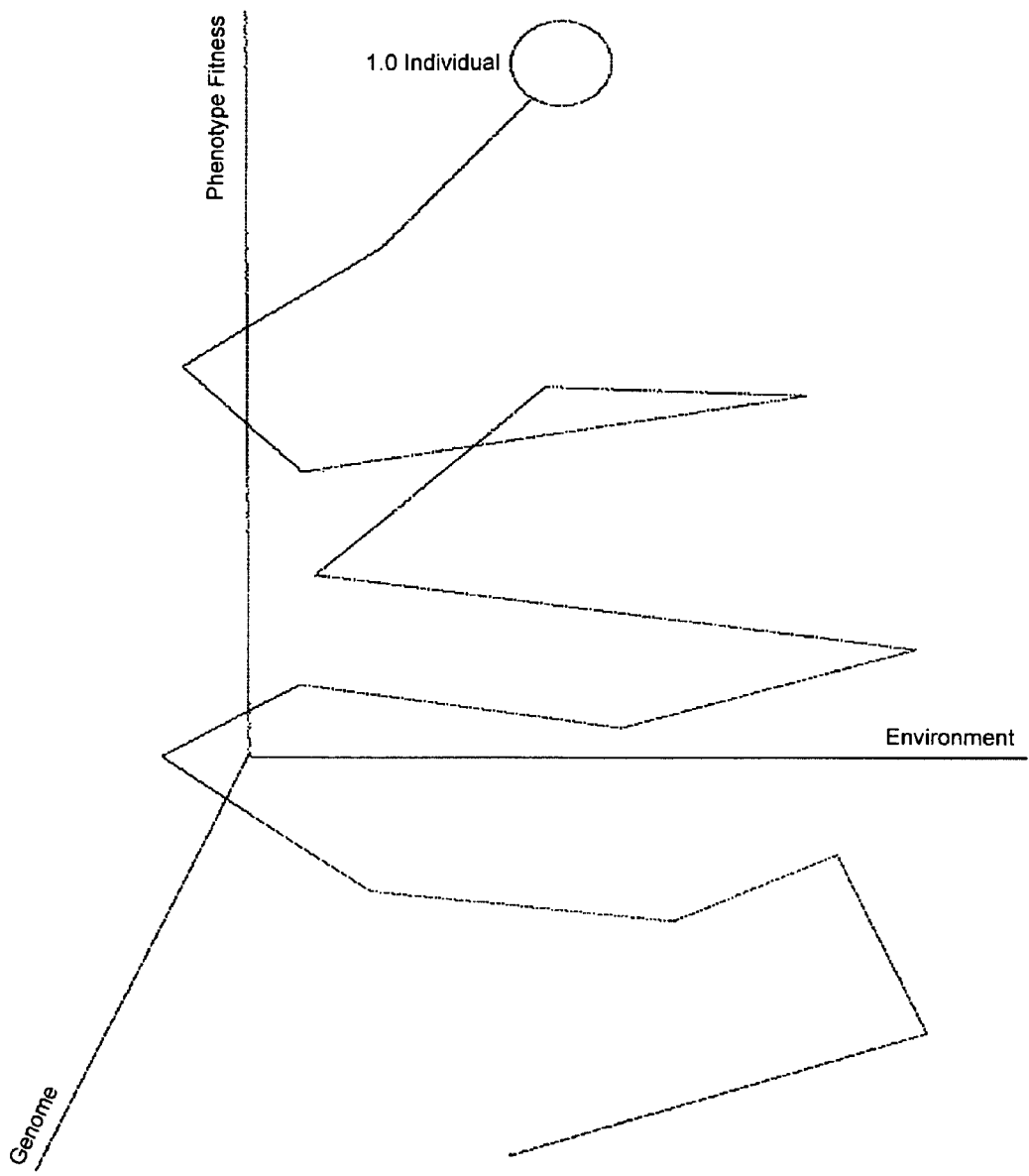
FIG. 4 is a diagram schematically illustrating the Evolutionary Search Space.

This evolutionary search using the evolution engine can be considered as a search through a search space. Such a search might be visualized as in FIG. 4. The drawing shows the importance of interaction between the genome and its evolving environment in the present invention's method of evolutionary search toward a phenotype fitness value of 1.00.

Due to the nature of evolutionary searches, movement through the search space is highly erratic. Depending on the replacement method used, the current best individual may not be replaced for many generations or a rapid succession of replacements may occur. The new best individual may be a radical improvement over its predecessor or may only slightly improve on it. Depending on the replacement method, it may even have lower fitness than its predecessor. However, selective pressure drives the best individual (and the population as a whole) toward improved phenotypic fitness over time.

Encoding a 64-Cell Cube with Emergent Self-Repair

Figure 5:
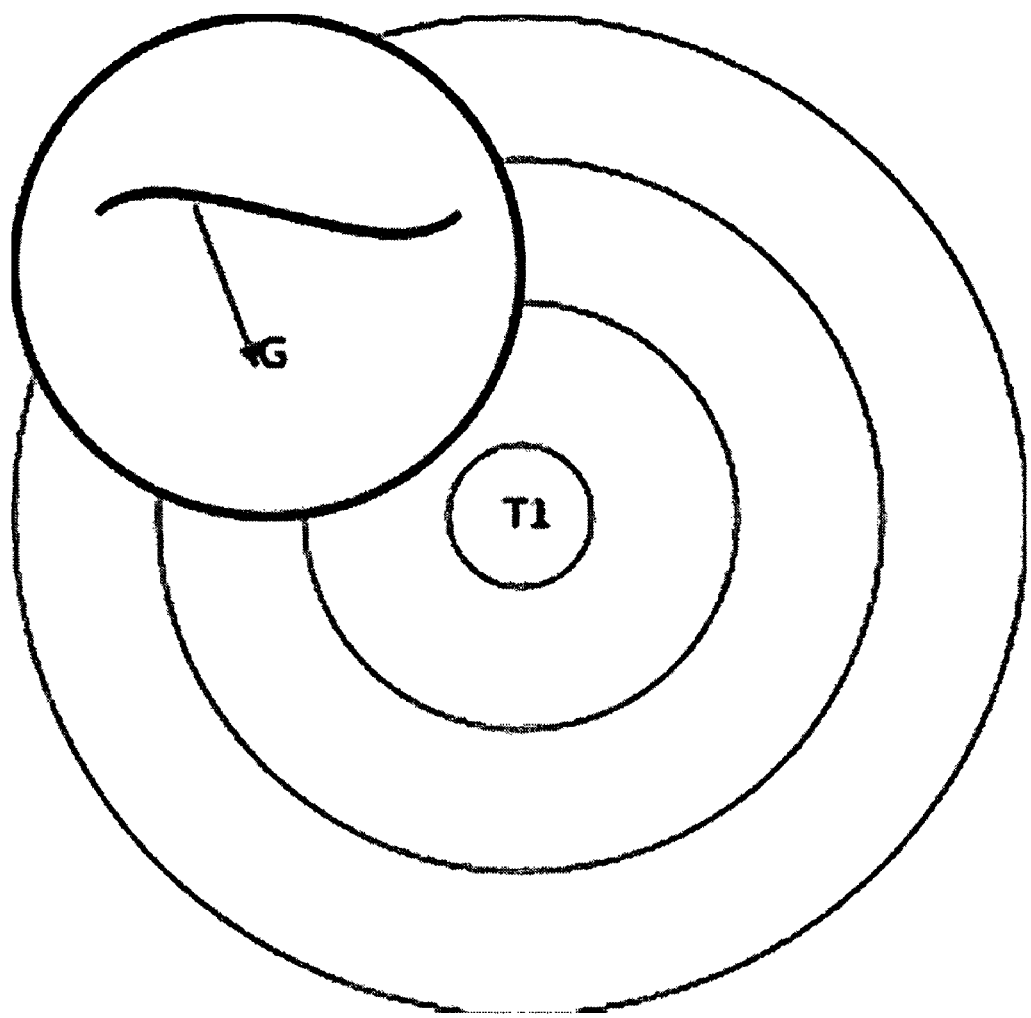
FIG. 5 is a diagram schematically illustrating a Single Cell with Molecular Source.

The example illustrated in FIG. 5 shows how the present invention can encode a simple shape, a 64-cell cube, with capability for emergent repair. Accordingly, the fitness of an individual is a function of how closely the stable configuration of cells matches the target shape. To produce more complex tissues, other target properties such as elasticity, connectivity, reactivity, contraction, and cellular state of differentiation must be incorporated into more complex fitness functions. The primitives, genome, and rules needed to produce such a virtual tissue are minimal, and other tissue shapes require more elaborate configurations, especially with regard to cell signaling parameters. However, the basic functions of the ontogeny and evolutionary search engines are as described above.

With a 4×4×4 cell cube as the target tissue shape, the developmental engine was initialized with a population of 50 individuals, each having a genome and initial configuration. Each individual's starting genome was a single gene with two control regions, one promoter and one repressor, linked to a single structural region coding for cell growth factor. A single, focused molecular source T1 in the environment promotes production of growth molecule G as shown in FIG. 5. The diagram shows the beginning of the first cell as placed in its environment near the molecular source.

Figure 6:
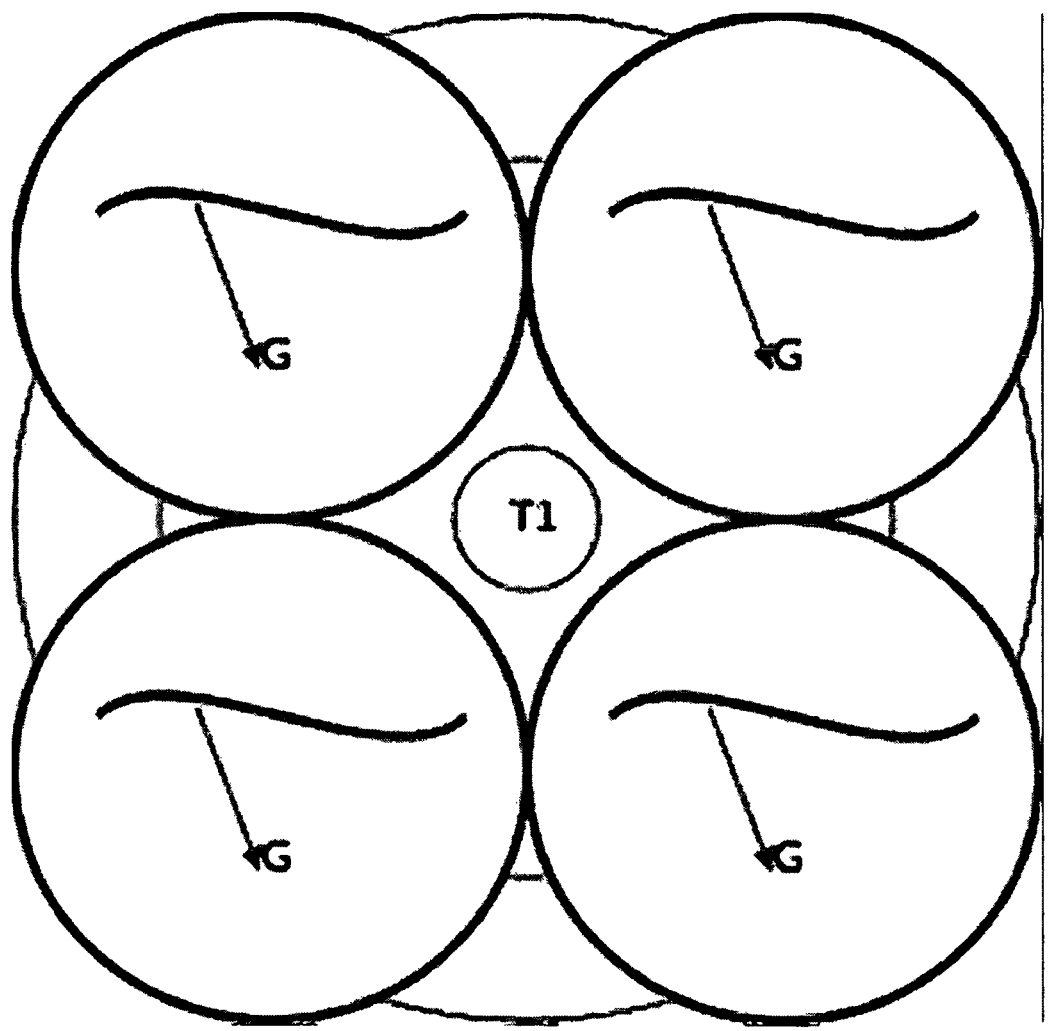
FIG. 6 is a diagram schematically illustrating Stage Two Cell Division of the 64 Cell Cube.

As the concentration of G passes the threshold for division, the cell divides. This build-up and division repeats until the area of highest concentration is filled as in FIG. 6.

Figure 7:
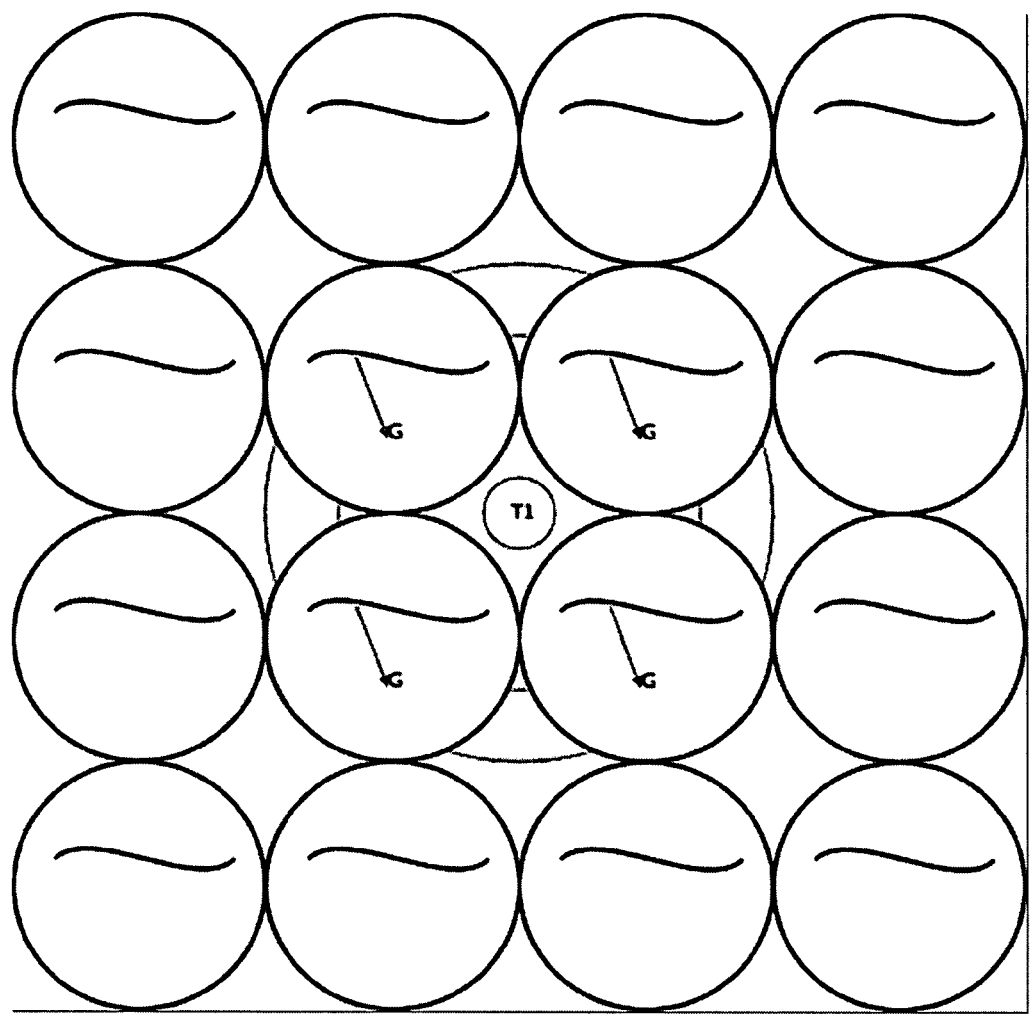
FIG. 7 is a diagram schematically illustrating Cell Division Outside the Area of High Molecular Concentration.

As each cell builds up concentration of G past the division threshold, it now divides into available adjacent positions outside the area of high molecular concentration in the environment until all adjacent positions are occupied as in FIG. 7.

Because the new perimeter cells are outside the effective range of influence of the molecular source, they never build up a sufficient concentration of G to divide. Because there are no available positions adjacent to the core cells, they are prevented from dividing, even though they may have sufficient concentrations of G to do so. This dynamic tension remains until an external event causes a change in the situation.

Figure 8:
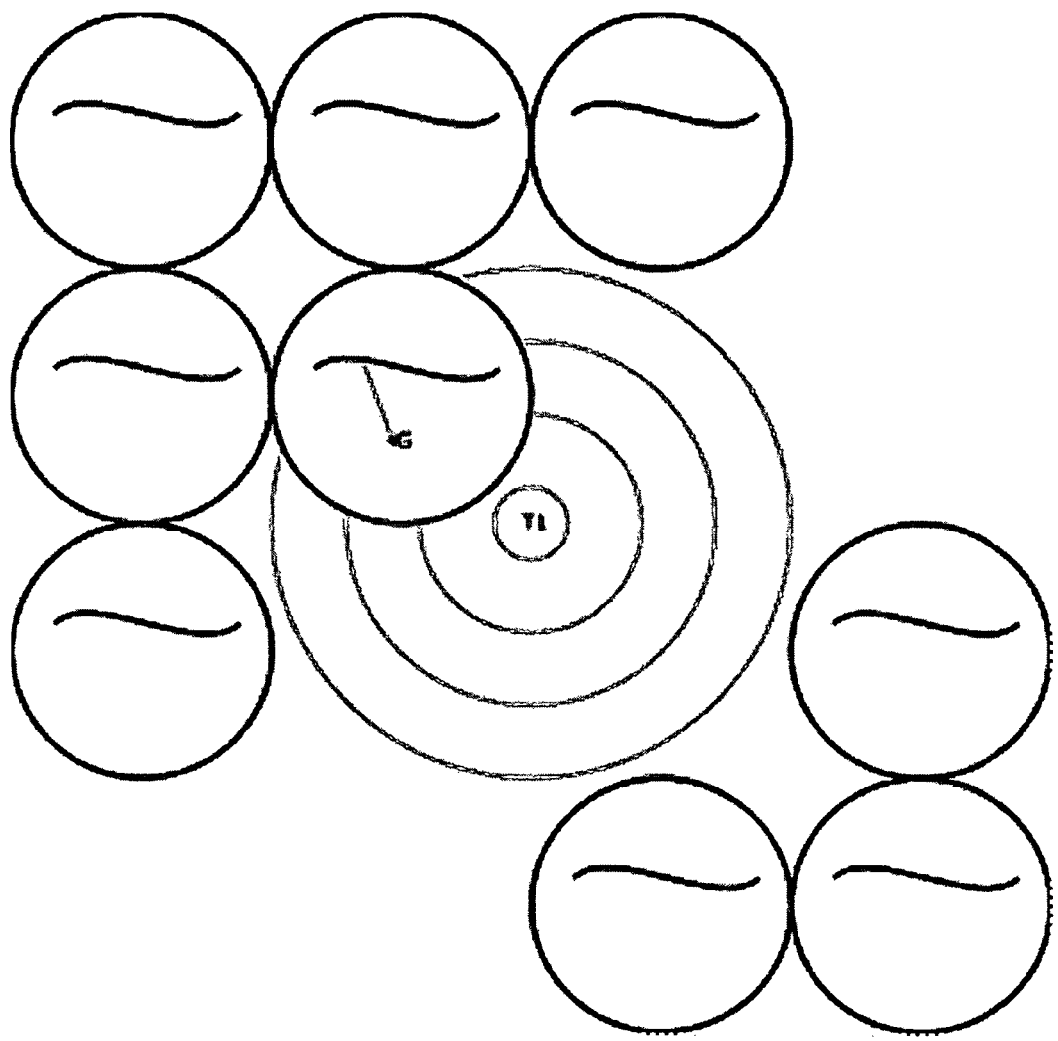
FIG. 8 is a diagram schematically illustrating Cell Injury Within the Cube.

When an injury occurs, removing some cells from the individual as in FIG. 8, core cells ready for growth will eventually replace all damaged cells. As long as a single core cell remains, complete self-healing of the individual can be accomplished.

The evolutionary search method of the present invention was configured with 14 different types of mutation operators, most of which alter the control and structural regions of the cell's genome, modifying parameters that dictate the type of molecule a particular control region interacts with, the effect of this interaction on transcription, and the type(s) of molecule(s) encoded by the structural region. The other mutation operators modify the placement and concentration of molecules in the environment. The mutation rate varies between 10 and 20 percent.

The best individual in the starting population had a fitness of 0.37 (fitness=1.0 indicates a perfect match). Fitness remained constant until the 19th generation, when an individual of fitness 0.64 was produced. At this point, the best individual's genome and the starting configuration had been modified extensively by mutation, with relatively large changes in the parameters governing interaction of the gene control regions, and addition of 4 point sources of growth molecules to the environment. Over the next 31 generations this evolutionary method produced incremental improvements to the average fitness of the population, until at the 50th generation the present method converged to a perfect solution, and the search terminated.

The left-most image of FIG. 9 depicts the best individual virtual tissue cube (fitness=1.0) thereby evolved. The drawing shows the 64 cell cube, as seen by the Visualization Engine, undergoing cell damage and subsequent repair.

The virtual tissue matches the target shape, but in addition, it is capable of sustaining a relatively large amount of damage to its structure during development without compromising its ability to produce a stable cube. The fully formed cube has a remarkable capacity for self-repair: even after 63 of its cells are destroyed, the 64-cell cube can regenerate itself perfectly from a single core cell. Although the undisturbed cube appears static, injury reveals that the capacity for self repair remains latent.

The capacity for self-repair in the virtual tissues produced by this invention arises from the interactions of particular rules and primitives, and so this functionality satisfies a simple objective definition of emergence:

it involves interactions of cellular primitives, it is not encoded in any single rule or primitive, it arises at a supra-cellular level of organizational hierarchy, and in the limited virtual environment of these embryos, it is useful (adaptive).

Self-repair arises from the underlying dynamic and continual development rather than from any explicit and imposed formulation. In the current implementation, four rules or primitives contribute to emergent self-repair in the 4×4×4 cube embryos:

the neighborhood definition for cell division (where new cells may be placed),
the definition of growth by cell division,
the threshold concentration of growth substance defined for that individual, and
a rule that existing cells may not be displaced by new cells, similar to the phenomenon known as 'contact inhibition' in living (non-cancerous) cells.

The stable cube shape results from a dynamic tension between conditions that promote growth (a local concentration of growth molecules above threshold for cell division), and conditions that prohibit or limit growth (all adjacent locations in a cell's neighborhood are already occupied). Thus, many cells in the cube embryo are poised for growth in a kind of stasis or balance, and loss of cells disturbs the balance, temporarily shifting it toward growth until a new balance is restored.

The ability to repair damage was not part of the criteria used to select fit individuals. In fact, the only fitness criterion was shape, a 4×4×4 cell cube. Therefore, while it is true that the cube shape is produced by specific arrangement of lower-level elements, the cells, what is interesting and emergent is the ability of such cubes to restore their configuration if they are damaged. Interaction of rules in specific conditions thus produces a stable cube shape and loss of cells induces self-repair, a behavior that is interpreted as resilience to damage, a component of robustness.

Encoding More Complex Forms

Figure 10:
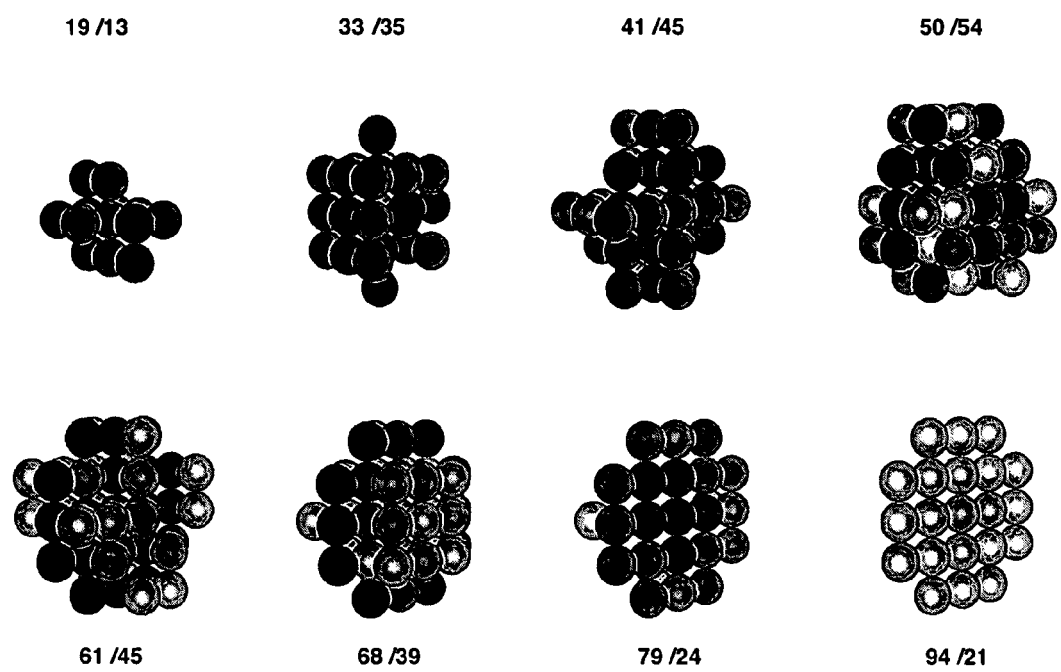
FIG. 10 is an illustration of growth stages of a 5×5×1 sheet embryo.

The genome that produced the 64-cell cube involved only genes encoding growth molecules, and no death genes or cell signaling was needed. To investigate the utility of cell death (apoptosis) and cell signaling for more complex schemes of development, the ontogeny engine was used to produce single- or multi-layered sheets of cells. Some of these develop by a more complicated process that involves cell signaling to cause death (apoptosis) of cells in undesired positions and to terminate cell growth at the appropriate time. For example, one individual during the early stages of development looks rather lumpy, but later the cells on either side of the embryo's medial plane die off, leaving a stable 5×5 single-layer sheet of cells as illustrated in FIG. 10. The drawing shows various time steps of the development from a single cell into a perfect 5×5×1 sheet of cells. Of particular interest is the "pruning" of unnecessary cells during development of the phenotype, which is a biologically appropriate phenomenon. In this case, incoming signals from neighboring cells induce other cells to adopt a state that stabilizes the sheet, but also inhibit the ability to repair damage to the sheet. Consequently, this individual is not as resilient to damage as the 64-cell cube. Nevertheless, while the sheet embryo is in the growth/development phase, it can sustain moderate damage yet still produce the desired target shape.

Figure 11:
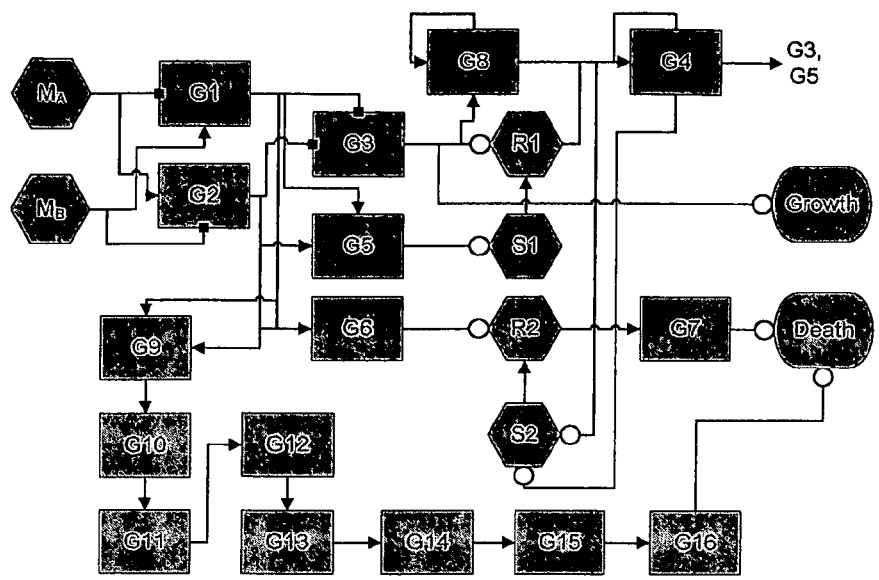
FIG. 11 is a diagram schematically illustrating Gene network for the sheet embryo, showing the relationship between genes, molecules, receivers, senders, resulting stimulatory and inhibitory effects and substances produced.

A network of molecular and gene interactions produces the 5×5×1 sheet embryo. As depicted in FIG. 11, the network involves 16 genes, 6 molecules ($M_A$, $M_B$, R1, R2, S1, S2) and three cellular actions or states (growth, stasis, or death). For example, activity of Gene 3 (G3) leads to production of R1, activation of G8, and growth. In turn G3 is controlled by G1 and G2, such that if neither G1 nor G2 is active growth is stimulated, but if either G1 or G2 is active growth is inhibited. As outlined below, activation of either G1 or G2 has two outcomes: 1) a complicated pattern of gene interactions that causes apoptosis through a combination of cellular signaling and 2) a delay mechanism that involves a sequential, daisy-chain stimulation of genes G9 through G16. This sequence takes some time to become established so death rates remain very low until about step 25. Genes G1 and G2 control a signaling pathway leading to the eventual death of cells on either side of the zone that forms the sheet. The interaction between molecules $M_A$ and $M_B$ and G1 and G2 defines a planar region where cells grow and survive, but outside of this plane cells eventually enter a state leading to death.

In addition to the timing delay, a secondary pathway for apoptosis is achieved through cellular signaling. When genes G1 and G2 are switched off, cells within the eventual sheet are stimulated to produce cell signal molecule S2 through a signaling pathway involving genes G3 and G8. Cells that are outside of this central sheet zone are stimulated to produce R2 via gene G6, triggered by either G1 or G2, and signal S1 is produced via gene G5. Cells within the sheet zone produce receptor R1 and signal S2. The interaction of these two signaling pathways (S1 to R1 and S2 to R2) causes cells within the sheet to signal cells that are outside of this zone to die.

To produce a stable sheet only one cell layer thick its growth must be terminated. This is achieved through a combination of cellular signaling and a feedback loop involving G4. Initially, cells within the sheet are stimulated to grow by activity of G3. As the cells in the sheet grow, they create a transient population of cells that produce S1, which activates receptor molecules R1 of cells in the sheet, which in turns stimulates gene G4. Once G4 is stimulated, a feedback loop is initiated that permanently ramps up production of a transcription factor that shuts down G3, terminating cellular growth. Thus, G4-mediated activity of cells outside of the sheet is critical to stabilizing the sheet.

Once G4 is activated, nothing can curtail its activity. Activation of G4 can be thought of as a mechanism of differentiation because it causes a permanent change in the pattern of gene expression. Before G4 is activated cells within the sheet are growing, and significant damage to cells in this layer does not affect the ability of the embryo to repair the damage and produce the target shape. However, after G4 activity reaches a certain level, then damage to cells in the sheet is much more likely to lead to permanent damage in the embryo, and after complete stabilization of the embryo, it is unable to repair damage because its cells can no longer divide.

Gene activity profiles for genes G3 and G4, which control growth of the sheet, reveal that increases in G4's activity (at ~step 75) are followed by a sharp decrease in the activity of G3 because of the strong inhibitory effect that G4 has on G3. Since G3 is responsible for growth, G4-mediated inhibition overwhelms all other input to G3 and completely terminates the growth of the sheet cells. Furthermore, G4's activity becomes self-sustaining through positive feedback, so termination of growth is permanent.

Genes G7, G9, and G16 are all involved in pathways that lead to cell death. The activity of G7 is directly controlled by a cellular signaling pathway that involves signaling molecules S2 and R2. The primary pathway that causes pruning of the embryo via apoptosis involves genes G9 through G16 in a cascade of gene interactions that leads to elevated activity of G16 and eventual death of cells outside the sheet. By comparison, the cellular signaling pathway involving G7 is weaker and contributes relatively little to apoptosis.

Evolving Other Target Shapes with Emergent Repair

Using other starting genomes and configurations, the invention has been used to evolve tissues with different shapes, such as hollow tubes and spheres. While not all of the virtual tissues so produced can repair damage during all phases of the development process, all of the shapes exhibit some ability to repair damage, depending upon the time the damage is introduced. Furthermore, different shapes have evolved different mechanisms that support emergent repair using different sets of primitives.

DESCRIPTION OF PREFERRED EMBODIMENTS

The embodiment of the present invention is described in terms of both the method of model generation and the characteristics and behaviors of the model resulting from that method of generation. The model generation may be performed using the combination of an evolutionary engine and an ontogeny engine. Once the model has been generated, it may be examined using the same ontogeny engine with a visualization engine. Such examination allows behavior of the resultant model to be reviewed and manipulated.

Figure 12:
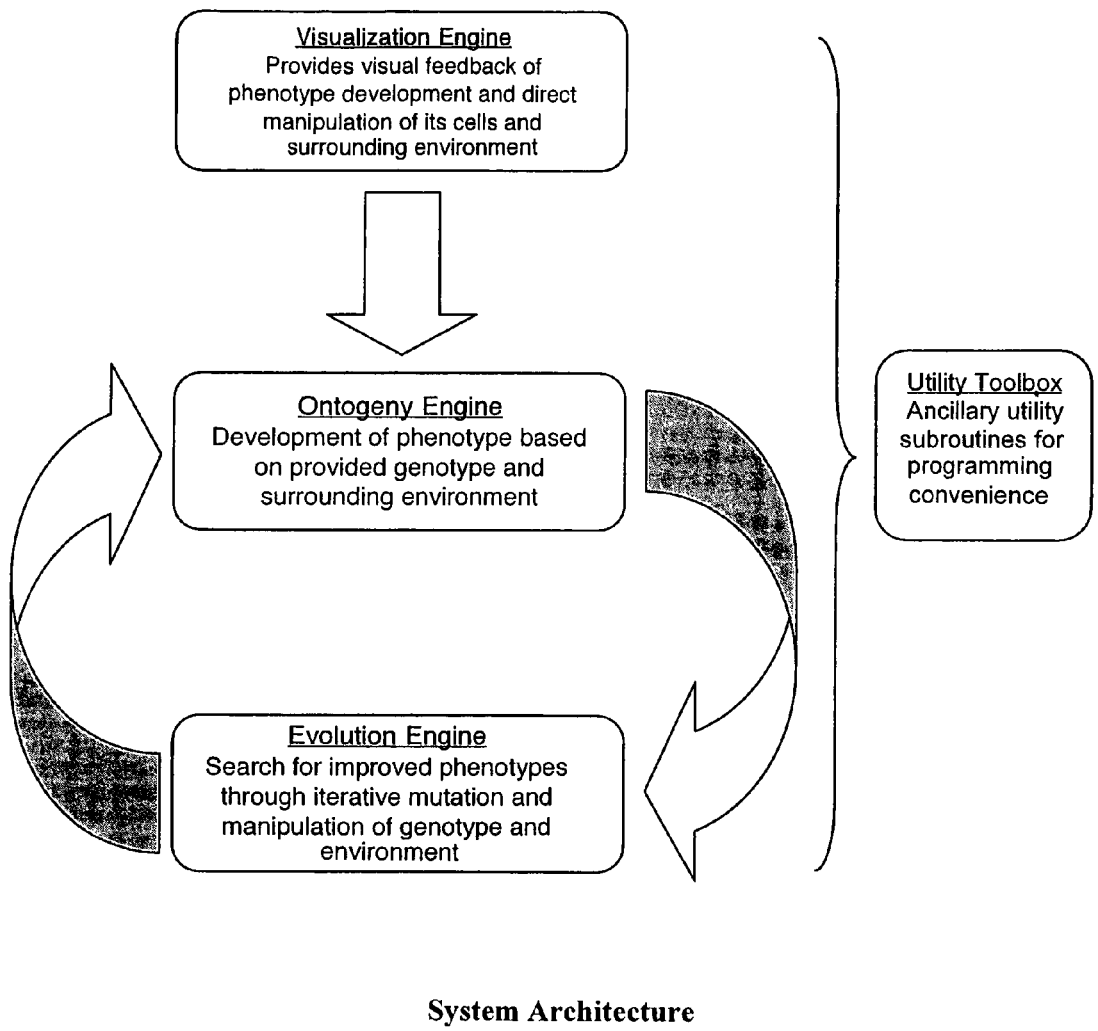
FIG. 12 is a diagram schematically illustrating Major Software Components of the System, showing the main components of the system's architecture.
Figure 13:
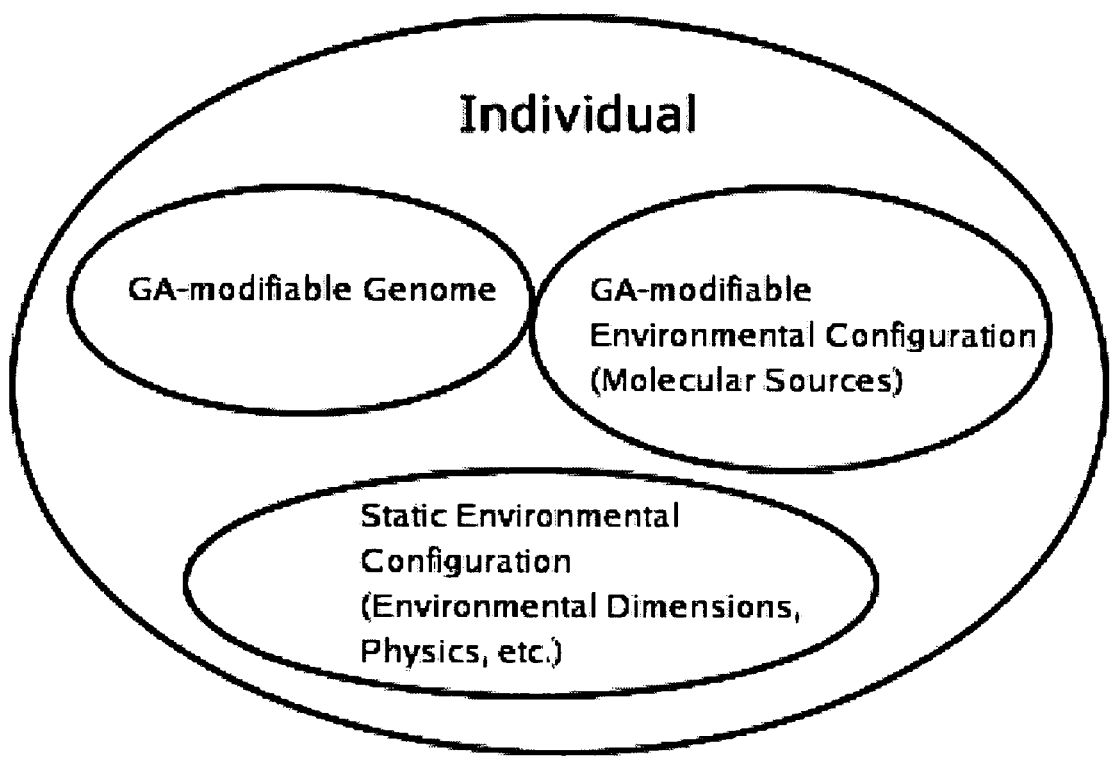
FIG. 13 is a diagram schematically illustrating a General Description of the "Individual" and its parts.

System Architecture:

The architecture of the present invention makes use of the ontogeny process described previously. A phenotype is continuously developed through the ontogeny engine from a genome and environment, the pair of which has been evolved through the evolution engine (GA). During this continued development, from its first cell through its maturation (i.e., stability) and beyond, it can be perturbed via the visualization engine where cells can be directly killed or indirectly by use of a virtual projectile that is fired upon the phenotype. For software engineering economy, an ancillary utility set of routines is applied. FIG. 12 shows the relation between the software components, the largest of which are referred to as engines.

The evolution engine of the present invention follows roughly standard evolutionary computing techniques. However, three features are noteworthy as a departure from prior art:
- avoidance of crossover as a technique for producing offspring (i.e., asexual reproduction) instead relying on numerous mutational operators frequently applied,
- development of the phenotype via the ontogeny engine as a prerequisite to the fitness evaluation, and
- direct evolution of the environment rather than only directly evolving the phenotype.

The available mutational operators affect a range of details regarding the genome or the environment conditions:
- mutation of any genome component value
- mutation of genome by gene duplication
- mutation of genome by internal gene shuffling (not crossover)
- mutation of genome by gene deletion
- mutation of any environment molecule production component value
- crossover of environment molecule production values The high-level algorithm of the Procedure "Evolution-Engine" for the evolution engine is shown below in Table D:

TABLE D

Procedure Evolution-Engine Pseudo Code

Procedure Evolution-Engine:
  prepare population with randomly-initialized individuals
  call Assess-Population TABLE D-continued Procedure Evolution-Engine Pseudo Code while population-has-no-fit-individuals
    select parents from assessed individuals
    for-each selected-individual
      stochastically mutate individual to form offspring
    end-for-each
    update population with offspring
    call Assess-Population
  end-while For purposes of the evolution engine and the ontogeny engine, an "individual" is considered to be the entire configuration that results in a phenotype when running the ontogeny engine. This "individual" consists of three parts: the GA-configurable genome contained in all cells, the GA-configurable environmental parameters such as molecular sources (i.e., gradient builders) in the environment, and the static environmental configuration including such parameters as environmental dimensions and environmental physics. The diagram in Figure B illustrates the individual and its three parts.

Changes to any of these parts would alter the resulting phenotype developed in the Ontogeny Engine and, therefore, none of them can be removed in consideration of the individual. As stated previously, development of the phenotype via the ontogeny engine as a prerequisite to the fitness evaluation, and so leads to the following fitness approach shown below in Table E. The table shows a high level outline of the Procedure "Assess-Population".

TABLE E

Procedure Assess-Population Pseudo Code

Procedure Assess-Population:
  for-each individual ( individual = genotype + environment)
    phenotype = Ontogeny-Engine(individual)
    fitness = Assess-Phenotype(phenotype, target-phenotype)
  end-for-each The ontogeny engine exploits the principles of genetic expression and regulation as the mutual interaction of the genotype and the developing phenotype. It also exploits the environment as a source of energy (via nutrients) for the phenotype and as a landscape for additional virtual-molecular manipulation This manipulation is accomplished by employing the concept of cell signaling which is in part used to influence cell division and death. While some previous art has considered cell signaling, their reliance on the resulting environment is an adjunct feature rather than a key contribution to the discovery of fit models. The lack of mutating the environment or directly manipulating it as peer component of the model's foundation results in a result that is simplistic in comparison to that of the instant invention. [Eggenberger, 1997, 2003].

TABLE F

Ontogeny Engine Pseudo Code

Function Ontogeny-Engine(individual) returns phenotype:
  initialize environment with nutrient sources
  place cell (with internal genome) into environment
  while (if visualized, then until-infinity, else until-stable)
    distribute cell-signals among cells and environment
    for-each cell in environment

TABLE F-continued

Ontogeny Engine Pseudo Code

```
        if asynchronous-stimulation-received-to-die
            remove cell from environment
        end-if
        transport presented molecules from environment into cell
        transcribe and express genes
        process presented signals
        if stimulated-to-die
            remove cell from environment
        end-if
        if stimulated-to-divide
            add copy of cell to environment
        end-if
    end-for-each
end-while
```

The high-level algorithm for the ontogeny engine is given in the preceding table, Table F, which shows in particular a high level description of the "Ontogeny-Engine" Function that returns the phenotype for an "Individual".

The algorithm makes use of cell signaling, molecular transport, and environmental influences in its development from the first cell's genotype to its eventual stable state (defined as a period without cellular growth or death).

The current implementation of the algorithm for assessing the fitness of the resulting phenotype is as shown in Table G below:

TABLE G

Fitness Evaluation Pseudo Code.

```
Function Assess-Phenotype(phenotype, target-phenotype)
returns fitness:
    score = 0
    for-each discrete-position-in-environment
        if target-phenotype has a cell in position
            if phenotype has a cell in position
                add 2 to score
            end-if
        else
            if phenotype has a cell in position
                subtract 1 from score
            end-if
        end-if
    end-for-each
    normalize fitness from score to be between 0.0 and 1.0
```

Table G, above, shows a high level outline of the Function "Assess-Phenotype", wherein the resulting phenotype returned from the call to Function "Ontogeny-Engine" (Table F) is measured against a target phenotype (objective function) resulting in a score ranging from zero to 100 percent (1.0 being a perfect match of the resulting phenotype of an "Individual" to that of a target phenotype).

Other implementations and algorithms of the Assess-Phenotype function are possible such as different point systems using the cell-map technique described above. More radical implementations include use of shape distributions [Osada, et al., 2002] or shape spaces [Zhang, et al., 2003]. Fitness can be any measure of the phenotype including one as simple as shape or more complex including functional traits.

During visualization, the ontogeny engine is run directly and continues until halted by the user. Thus the user can perturb the model after it has reach stability. In doing so, many phenotypes exhibit the emergent behavior of self-repair from most injuries wherein the phenotype restores the removed cells without external intervention or instruction: this behavior is not directly coded for in the algorithm. This demonstration is not possible under higher-order specifications through deterministic mathematical formulae and yet is necessary for tissue modeling with any degree of fidelity.

System Construction:

The present embodiment of the system makes use of two main functions that involve the engines as appropriate: search for a model (evolution+ontogeny) and work with that model (ontogeny+visualization).

csga:

Model search is invoked through the command "csga". csga is used to evolve a starting virtual genetic description to match a given target phenotype description. This process employs genetic algorithms to repeatedly mutate and then assess the fitness of various genetic combinations until the match is found.

csga works by reading in a configuration file, written in XML, that identifies an initial population of virtual cellular individuals and various genetic algorithm parameters, including the specification of a target individual. From that configuration, csga internally generates then evolves the given individuals until the one matching the target is discovered or until another limiting statistic is encountered. During the csga run, various information is written to an output stream upon every evolved generation. This output information can be made more or less verbose by configuration settings. A csga run that results in a fit individual can be configured to provide the detailed information for that individual as part of the output for the last generation in the run.

csga requires a large set of parameters to set specific evolutionary behavior and provide it with initial data to start the evolution from. Currently, these parameters are supplied at the beginning of an evolutionary run through an "extensible markup language" (XML) file. An evolution run is started by invoking csga with the command csga and a parameter giving the filename of the XML configuration file.

Once csga has read in the configuration file, it will begin an evolutionary run based on that supplied configuration. Assuming the configuration is valid, the evolutionary engine will be applied according to the configuration. The general intent when configuring csga is to specify an environment, a population, and limiting factors that launch and then govern the subject evolution.

At each generation during the run, an XML stream will be updated to provide statistics (requested in the configuration) regarding the run itself and the updated individuals in that generation. When a limiting factor is reached (e.g., maximum fitness, maximum steps), processing will cease and the XML stream will be closed.

Therefore, the output XML stream can be redirected for saving into serialized file for later analysis. Further, individual configurations (i.e., <CsIndividual>) can be extracted manually for input into other applications beyond or ancillary to the present invention. Other output generated by csga during the evolution may be processing warnings (e.g., deprecated configuration parameters used) or processing errors (e.g., unable to parse XML configuration file).

The configuration for csgaview addresses several areas across the evolutionary engine, the ontogeny engine, and the display of information during the processing of those engines.

In detail, the configuration covers the following specific points and elaborated after this list:
- initial value to seed random calculations from
- whether to allow progress display during evolution
- choice of a distributed processing approach (for use when running on a computer cluster)
  - sequential, non-distributed processing
  - simple distributed processing with even portions of the population
  - distribution of individuals one at time to processors upon request
- starting population to initialize the evolutionary engine with
  - number of individuals
  - initial individual configuration
    - virtual genome
    - growth environment
      - discrete cell grid
      - continuous free space
    - cell signaling mechanism
    - gradient builders
  - randomizing operations to generate diverse starting population
  - fitness evaluation method specification
- culling selection criteria
- replacement specification
- mutation operators
  - point crossover for environment gradient builders
  - gene addition, duplication, movement, and reduction
  - direct mutation on genome elements and properties
  - direct mutation on gradient builder elements and properties
- processing limits
  - maximum generations to evolve through
  - maximum fitness measure to evolve to
  - maximum number of fitness evaluations to evolve through
- processing monitors for the generation of progressive output
- statistic specifiers for tracking metrics
  - average fitness
  - best fitness
  - evaluation count
  - evaluation time
  - fitness calculations
  - generation count
  - genetic history
  - individual information for all members of the population
  - individual information for the most fit member of the population
  - elapsed clock time When csga begins to evolve a population, it does so by starting with some initial individuals. As described above, these individuals are specified in the configuration file.

Every individual has virtual genetic signature referred to as a genome. This genome contains sets of values referred to as genes meant to mimic the function of genes in biological constructs. There are two kinds of genes: regulatory and structural.

Regulatory genes control whether and to what extent related structural genes are expressed. Based on the interaction between the molecules and the regulatory gene, the expression of the related structural genes may be promoted or inhibited. The severity of this effect is a function of a comparison of the genes' and molecules' chemical signatures. This comparison is referred to as their affinity for one another.

The specification for regulatory genes in the example embodiment are made up of two parts:
- a chemical signature that is comprised of two properties:
  - chemical indicant, or indicant for short, which refers to a consolidated chemical formulation appropriate for its context (e.g., in a genome, the consolidate chemistry would be that of a virtual nucleotide sequence)
  - sensitivity represents how attractive the indicant is to another indicant presented to it.
- effect limits or promotes transcription of structural genes based on molecule presented to the regulatory gene. This effect controls both the occurrence of transcription and the concentration of the resulting transcribed molecules.

Structural genes wrap prototype molecules to be produced during transcription. Therefore, the specification of a structural gene is the specification of the wrapped molecule. Such wrapped molecules have not only chemical signatures, but also molecule types and decay rate. The molecule resulting from transcription has a concentration that is determined from the regulatory gene.

A cell is affected by the molecules it encounters. So far these molecules affect whether a cell grows, dies, or produces more molecules in turn. These molecules may come directly from other cells in the course of cell signaling or they may come direct from the environment itself. Molecules that are to come direct from the environment within which the phenotype is grown are specified through gradient builders.

A gradient builder produces molecules at every step of the type specified. For an initial individual, a set of gradient builders may be specified. Each gradient builder defines the environmental distribution of a particular molecule type and has the following properties:
- a chemical signature that is comprised of two properties:
  - chemical indicant, or indicant for short, which refers to a consolidated chemical formulation appropriate for its context (e.g., in a genome, the consolidate chemistry would be that of a virtual nucleotide sequence)
  - sensitivity represents how attractive the indicant is to another indicant presented to it.
- coordinate describes the location of its peak concentration in the environment
- strength describes the peak concentration of molecule being distributed
- exponent describes how the concentration weakens with distance from the coordinate Under the ontogeny engine, every individual is to be grown within an environment that gives it context. The simplest environment supported in the current embodiment is a discrete space referred to as grid space or a cell grid.

The grid space assumes that each cell is of uniform size and occupies a uniformly sized space within the grid. That is, the environment is a fixed, three-dimensional grid that has discrete locations for cells to occupy. While this approach limits the flexibility by which cells can be placed, it does provide a direct and simple way to work with simpler structures to quickly evolve and assess their success.

The following are required to be specified as part of the configuration:

Dimensions: three values to give the overall size of the grid. For instance, a grid that could handle an 8×8×8 cube at a maximum would be specified as 8 wide, 8 tall, and 8 units deep.

Cell placement: upon cell division, the new cell needs to be placed somewhere in the environment; this specification allows rules to be configured for that placement. These configurations describe constraints or preferences to be followed when placing cells. These configurations may be combined as desired.

Constraints: if a constraint cannot be met upon cell division, the division is not allowed to occur. Currently two constraints are available:

AllAdjacent: each cell added as a result of cell division must be placed in a grid location that is immediately adjacent to its parent cell.

Vacant. each new cell may only be added to a grid location where no other cell is currently located.

Preferences: currently one preference configuration is available:

HighConcentration: each new cell added as a result of cell division is attempted to be placed at a location where the current highest concentration of environmental molecules can be found.

Cell signaling allows cells to exchange molecules to influence one another's behavior. Currently only one model of signaling is supported The local model supports the following signaling behavior:
specification of a neighborhood to represent a cell's association with others for signaling. Currently, only an All-Adjacent neighborhood is supported.
production of sender molecules to indicate a cell's propensity for signaling another cell
production of receptor molecules to indicate a cell's propensity to receive a signal and to also indicate how a cell's state should be changed as a result of receiving the signal Physics: the environment provides for the description the calculations that can take place during the growth of a phenotype.

Affinity Evaluator evaluates the affinity between chemical signatures of molecules or genes. In general, affinity is greater the closer two chemical signatures are measured to be. Currently two formulae for measuring how close the chemical signatures are supported:

DefaultAffinity calculates affinity to be greater as the difference between the involved indicants is smaller. The affinity calculated is made proportionate to that difference through the sensitivity property.

This calculation is given by $$e^{((-s_1 s_2)(i_2 - i_1)^2)}$$

where the subscripts 1 and 2 denote which of the chemical signatures is being referred to, is the sensitivity of the corresponding signature and i is the indicant of the corresponding signature.

SmoothAffinity is similar to default affinity but tempers the effect of differences in the indicants to result in a more continuous degradation. After further experimentation, it has been discovered that this affinity has had a counterintuitive effect on the calculation of the affinity. This calculation is given by $$e^{(-\frac{1}{2}(s_1 + s_2)|i_2 - i_1|)}$$

where the subscripts 1 and 2 denote which of the chemical signatures is being referred to, is the sensitivity of the corresponding signature and i is the indicant of the corresponding signature.

Promotion is a measure of the degree to which the structural gene expresses its wrapped prototype molecule. The Promotion Evaluator determines that promotion based on the concentrations of the presented molecules, the corresponding regulatory gene's measured affinities to those molecules, and the regulatory gene's effect value.

In calculating the promotion, the corresponding regulatory genes' measured affinities to the presented molecules are totaled. This total affinity value is used as a term in the remainder of the calculation.

DefaultPromotion causes molecules to be expressed at a constant, given rate if the following are true:
total affinity is beyond a provided threshold, and
the summed regulatory genes' effects are more than a provided threshold.

Therefore, this promotion specification takes three parameters:
affinity threshold: the value the total affinity must meet or exceed for expression to occur,
promotion threshold: the value that the summed effects must meet or exceed for expression to occur, and
active concentration: the rate at which molecules are to be expressed.

SmoothPromotion causes molecules to be expressed as a proportion of a specified promotional value. Therefore, even at very low affinities, there may be some promotion applied to expression.

Specifically, the rate of expression is $$r = \begin{Bmatrix} ap, & p > 0 \\ 0, & p \leq 0 \end{Bmatrix}$$

where r is the rate of expression, a is the maximum promotion rate, and p is the proportion of that rate which is calculated from the following formula:

$$p = \sum_i \left( \frac{f_i}{1 + e^{t-m}} \right)$$

where $f_i$ is the effect of the i-th corresponding regulatory gene of expression, t is the total affinity of the corresponding regulatory genes and m is the given midpoint of the sigmoid function $$\frac{1}{1 + e^x}.$$

Therefore, this promotion specification takes two parameters:
promotion midpoint: the amount by which to shift the sigmoid midpoint relative to the total affinity of the corresponding regulatory genes, and
active concentration: the maximum rate at which molecules are expressed.

Initial individuals do not exist by themselves but rather are described as part of a population. In its simplest form, a population is simply a collection of individuals, separately described.

However, having to write a separate description for the hundreds of individuals that might exist in a population is a tedious and error-prone task and so csga accepts some additional population specifiers.

Recursion: Populations may be recursively defined; that is, a population may contain one or more subordinate populations. In this way, large, diverse, but structured populations may be quickly built up in the specification.

This feature also allows the simple merging of a smaller populations into large populations, a feature that in the future is expected to make it easier to recombine populations distributed for separate evolution.

Multiplier: A multiplier allows the multiplication of all the specified individuals in the population by a given factor. For example, if a multiplicand of 5 is specified, then five of each specified individual will be generated as part of the initial set. Thus, the simplest way to define a uniform set of individuals in a population is to specify one individual in detail and then give a multiplier to the number of those individuals desired.

Repeat: This specifier causes a set of mutation operators to be repeatedly applied to the subject population's individuals for the number of times that the repetitions specifier gives. These mutation operators are the same full range of mutation operators that exist for the evolution overall. Use of this Repeat specifier allows a diverse population to be quickly specified from a uniform specifier. Therefore, when used in conjunction with the Multiplier specifier and the recursive feature of populations, large diverse populations can be built up simply.

A main function for a genetic algorithm is to evaluate its individuals and determine which ones have been the most successful and then to cull out individuals to create a selection-by-survival dynamic in its processing.

In the evolution engine, fitness is determined by applying the ontogeny engine to produce a stable phenotype then review it to see how well it meets the fitness criteria. The fitness criteria currently supported primarily consists of various fitness metrics and some processing limits on the growth simulation.

Two example fitness metrics are described here:
Absolute: an absolute comparison method that compares the candidate individual to an exacting target individual, cell by cell, to see if they match.
GradientCount: this method uses the same comparison as Absolute, but treats otherwise equivalent candidates as better if they use less gradient builders for their development.

A Maximum Steps value limits the total number of steps that the growth simulation performs regardless of any other factors. It essentially acts as a simulation governor.

A Stability value provides a measure of when a growing phenotype may be considered stable (i.e., when it is not expected to grow or die further). Currently, the only measure available for configuration is the number of steps without a change.

In evolutionary computing, selection is the process by which individuals are chosen to contribute their "genetic" values to the next generation. Currently, the only selection criteria recognized is a roulette selection.

Replacement refers to the process by which individuals in a population are replaced by their "offspring" to form the next generation. Currently, there are three, mutually-exclusive, replacement strategies available.

Generational: The parent population is completely replaced by the offspring population.

Generational with Elitism: The parent population is completely replaced by the offspring population except if no offspring individual is as fit as the fittest parent, that parent replaces the least-fit offspring in the new generation.

Merge and Reduce: This method allows the experimenter to specify the Merge method and the Reduce method. As of this writing, the evolution engine only provides CommaMerge for the Merge method and TruncationReduction for the Reduce method (these are the default settings for the MergeReduce replacement method). CommaMerge merges the parent population into the offspring population. TruncationReduction then takes these results and removes the worst individuals until the final population is equal to the original size of the parent population.

As part of the configuration, a target file is generally given so that the evolution can compare against an existing phenotype to assess how close it is to evolving to it.

Currently, the target file only specifies the number of cells, the cell locations (per the cell grid) that are filled with a cell, and the cell locations that are to be empty.

Every generation by the evolution engine allows for mutation of individuals' genomes and the environment in which they develop. Such mutation causes the resulting phenotypes to change slightly or dramatically and so affects their growth and ultimately their fitness. By choosing different mutation schemes, the speed and success which the initial population will approach the targeted individual specification is affected.

In theoretical computer science terms, this means that by beginning with the antecedent of the initial population, a search may be conducted to discover an individual specification that will perform well when put to the fitness test. This search can be quick if either the antecedent is reasonably close to the target or if the mutation operators cause the search space to be traversed most directly.

Each mutation operator may be wrapped by a probability specification. This specification, given as a value between 0.0 and 1.0, determines the likelihood that the wrapped mutation operator will be applied to a given individual during a single generation.

The following are the mutation operators currently available to the evolutionary engine:

Specific gene mutations: causes value components of a gene to be directly mutated.

Gene sequence mutators: causes individual genes to be copied, moved, or deleted from across a genome. Such mutations are homogenous: that is, regulatory and structural genes are not intermixed directly.

Gene assembly mutators: causes whole sets of sequences to be copied, deleted, or shuffled within a genome. This can cause dramatic changes in a genome.

Gradient builder mutations: both mutations of specific gradients is possible or across gradient builders as a collection, including the addition or subtraction of gradients from that collection. Each value component (affinity, sensitivity, strength, exponent, and location coordinates) can be directly mutated. Such a mutation can bound so that the mutation itself is limited in scope.

Gradient builder crossover-by-point: causes two individuals to trade gradient builders. Point crossovers do this by using the same index within each individual's set of gradient builders to use as the point where the gradient builders are cut and spliced from. In this example embodiment, this is done by randomly choosing a point with one individual's set of gradient builders, moving the end of that set to the end of the other individual's set at that same random point, and vice versa.

Many mutated values can be determined through the application of a statistical random distribution that affords some bias to the numbers. These distributions are limited to stay absolutely within a given interval through the specification of minimum or maximum values. The following are supported distributions:

standard normal distribution, where the z-value [i.e., $z=(X-\mu)/\sigma$] is specified:

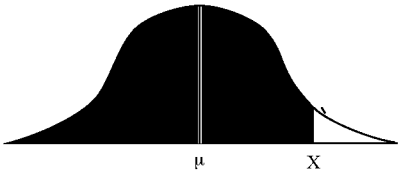

range distribution, where the distribution is uniform but the mutated value is constrained to be within a given absolute range with respect to the original value:

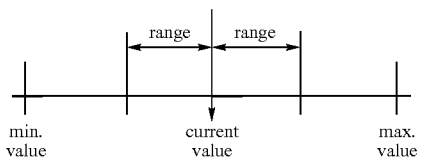

relative distribution, same as range distribution above, but the range is given as a percentage of the original value rather than a fixed value Additionally, each of these distributions may be applied as continuous functions or as discrete (integer-based) functions.

Without a completion criteria, the evolution engine would continue its evolutionary process indefinitely. Therefore, the configuration supports the following limits to allow the evolution to end upon meeting a specific criterion:

Fitness limit: Clearly if the evolution successfully produces the "ultimate" individual (in csga, that is an individual that exactly matches the target specification), there is no need to continue. Typically then, the fitness limit is set to 1.0 (i.e., 100% fitness). This can be lowered if desired, but higher specified values will be interpreted as if 1.0 were specified. Once any stable individual is discovered that has a fitness value that is equal to or higher than this limit value, the evolution engine will stop.

Generation limit: A limit on the number of evolutionary generations can be specified. Once the number of generations has been evolved as given by this limit, the evolution engine will stop.

Evaluations limit: A limit on the number of fitness evaluations can be specified. Fitness evaluations do not correspond directly to generations produced since each individual will be evaluated once in every generation it is mutated (or during the first generation). Once the number of fitness evaluations has occurred as given by this limit, the evolution engine will stop.

Various metrics can be recorded for each generation that csga processes. The following are some of the collectors of statistics that are currently supported in the example embodiment:

average fitness: the average fitness in the given generation across all of the individuals best fitness: the highest fitness in the given generation from across all of the individuals evaluation count: the number of fitness evaluations that have occurred so for in the evolutionary run evaluation time: the amount of clock time taken up so far in fitness evaluations only since the evolutionary run began fitness: a list of all the individual fitness values, in descending order, for the given generation generation: the ordinal count of the generation. Generation #0 is are the initial individuals before the run has begun the evolutionary process individual data node: the resulting individual information, suitable for use as input to csgaview or for initial individual specification, of the most fit individual for the given generation time: the overall clock time since the evolutionary run began csgaview:

Model visualization is invoked through the command "csgaview". csgaview is used to simulate visually the growth of a particular virtual genetic description. In this way, a particular phenotype, from growth to stabilization, may be directly examined graphically. csgaview is primarily intended to allow the visualization of any virtual individual, generally from csga. Therefore, csgaview takes as input a single description of a virtual cellular individual and then processes it step by step. User controls are given to provide some limited control of the processing. csgaview can be used to generate a target file which is a simple cell-map file that indicates what an individual looks like at a given step point (generally done after the individual has been grown to stability). csgaview can also be run without visualization so that it's processing statistics are written to a text output stream instead; this last feature can be useful for comparing the sequence for growth steps from one individual or processing logic to the next. This last capability is consider part of the visualization engine as well; it is considered a text serialization of visual rendering, somewhat like a script for a movie.

csgaview provides a visualization window into the growth of a phenotype from its genotype using the same ontogeny engine that powered the evolutionary fitness assessments made under csga. This visualization allows the user to examine what it means for a given phenotype to have a reported fitness against an already determined target, to quickly see what kinds of development defects it may have encountered, in its evolution, or to appreciate the behaviors of a developed phenotype.

The visualization makes use of a standard visualization software toolkit to fashion a simple interface for watching the simulation directly. Further, csgaview can run without visualization to create direct XML streams of the simulation in action. The latter is useful for automating simulation comparison tools.

csgaview requires only the parameters to describe an individual's genotype and the environment it is to develop under. Currently, these parameters are supplied at the beginning of a simulation through an XML file. The specific parameters available for configuration are the same as supplied for the initial individual specified in csga.

Once csgaview has read in the configuration file, it will begin a simulation of the development of the supplied cellular individual in its specified environment. Using the ontogeny engine, the phenotype will begin with a single cell with the specified virtual genome and add, change, or remove cells in each step according to the environmental influences (including influences created by other cells). The simulation continues indefinitely but there are controls available to the user during the simulation.

The main purpose of csgaview is to provide visualization of the subject phenotype's development. This visualization is intended to help the user's intuitive understanding of what is actually represented during the phenotypes maturation. In the example embodiment, virtual cells of the phenotype are presented presently by spherical shapes where each cell is colored blue if it is stable. A cell's color graduates to red as the urge to clone itself gains strength. Upon cell death, it is simply removed from the display.

Projectiles in csgaview act as virtual bullets, allowing the user to consider how an injury to the phenotype might be handled. It is depicted by a white triangle moving through the visualization field.

The graphics engine (VTK) used by csgaview for its visualization provides a wide range of effects such as rotation and zoom.

If a target "shadow" is requested, the virtual cells of the target are shown in the same way as the developing cells except that they do not change during the simulation and their color is a dark grey, thereby creating a shadow effect. The developing cells are considered in the foreground during simulation while the target cells are in the background relative to the developing cells.

During simulation, the user has a number of controls available to interact with the visualization and the underlying simulation:

Begin Simulation: initializes the simulation by seeding it with an initial cell and starts the phenotype development.

Pause/Continue: pauses or resumes the step-wise development of the phenotype; this is analogous to the user being able to "stop time" in the simulation.

Step: advances the ontogeny engine and the resulting display by the visualization engine by one time step.

Projectile: pauses the simulation, launches a projectile that will kill every cell it "touches", and resumes the simulation once the projectile has passed through the phenotype. This is intended to show injury to the phenotype and subsequent healing.

Exit: immediately ends the ontogeny engine and the visualization engine and terminates csgaview.

Kill Cell: when paused, allows the user to select a cell and immediately cause it to die. Upon resumption of the ontogeny engine, the cell's death will be immediately processed.

Write Target: pauses the simulation, generates an individual target file to match the simulated phenotype at this time-step, and resumes the ontogeny engine.

Under some circumstances, csgaview will produce text output streams of its results rather than provide direct visualization.

Target: produces a target file suitable for use as a reference shape for the fitness function during evolution.

Simulation steps: produces an XML stream that itemizes the cell locations during each step of the simulation. This allows automated comparisons to detect differences in the simulation process. This may be useful in determining how efficient a particular phenotype is in reaching maturity or to detect changes in caused by modifying the evolution engine.

The following table, Table H, is an example prototype of a configuration file used by csga to start the evolution engine:

The following table, Table I, is an example prototype of a configuration file used by csgaview to start the ontogeny engine for visualization:

TABLE I

```
<CsIndividual>
    <Genome>[[[1, 1] 1, [2, 1] -1] [[0, 0] G]]</Genome>
    <Environment>
        <CellGrid>
```

TABLE I-continued

```
            <Dimensions>[8, 8, 8]</Dimensions>
            <CellPlacement>
                <AllAdjacent></AllAdjacent>
                <HighConcentration></HighConcentration>
                <Vacant></Vacant>
            </CellPlacement>
            <CellSignal>
                <Diffusion>
                    <DiffusionGrowthRate>0.2</DiffusionGrowthRate>
                    <DiffusionKillRate>0.1</DiffusionKillRate>
                </Diffusion>
                <Local>
                    <Neighborhood>
                        <AllAdjacentNeighborhood>
                            <Radius>1.45</Radius>
                        </AllAdjacentNeighborhood>
                    </Neighborhood>
                </Local>
            </CellSignal>
            <Physics>
                <AffinityEvaluator>
                    <DefaultAffinity></DefaultAffinity>
                    <SmoothAffinity></SmoothAffinity>
                </AffinityEvaluator>
                <PromotionEvaluator>
                    <DefaultPromotion>
                        <AffinityThreshold>1</AffinityThreshold>
                        <PromotionThreshold>0</PromotionThreshold>
                        <ActiveConcentration>1</ActiveConcentration>
                    </DefaultPromotion>
                    <SmoothPromotion>
                        <PromotionMidpoint>0</PromotionMidpoint>
                        <ActiveConcentration>1</ActiveConcentration>
                    </SmoothPromotion>
                </PromotionEvaluator>
            </Physics>
        </CellGrid>
        <FreeGrid>
            <Dimensions></Dimensions>
            <CellPlacement>
                <AllAdjacent></AllAdjacent>
                <HighConcentration></HighConcentration>
                <Vacant></Vacant>
            </CellPlacement>
            <CellSignal>
                <Diffusion>
                    <DiffusionGrowthRate>0.2</DiffusionGrowthRate>
                    <DiffusionKillRate>0.1</DiffusionKillRate>
                </Diffusion>
                <Local>
                    <Neighborhood>
                        <AllAdjacentNeighborhood>
                            <Radius>1.45</Radius>
                        </AllAdjacentNeighborhood>
                    </Neighborhood>
                </Local>
            </CellSignal>
        </FreeGrid>
    </Environment>
    <GradientBuilders>[ ]</GradientBuilders>
</CsIndividual>
```

Under the <Genome> tag in the above XML, the notation for describing the values that make up a genome are as follows:

Genome: [GeneAssembly$_0$, GeneAssembly$_1$, . . . , GeneAssembly$_{n-1}$]

GeneAssembly: GeneSequence$_{RegulatoryGene}$ GeneSequence$_{StructuralGene}$

GeneSequence$_{RegulatoryGene}$: [RegulatoryGene$_0$, RegulatoryGene$_1$, . . . , RegulatoryGene$_{n-1}$]

GeneSequence$_{StructuralGene}$: [StructuralGene$_0$, StructuralGene$_1$, . . . , StructuralGene$_{n-1}$]

RegulatoryGene: [Indicant, Sensitivity] Effect

StructuralGene: Molecule

Molecule: [Indicant, Sensitivity] MoleculeType
   or if Type=R:
      [Indicant, Sensitivity, TargetIndicant, TargetSensitivity] MoleculeType Molecule Type:
   G (Growth)
   K (Kill/Death)
   T (Transfactor)
   S (Sender)
   R (Receptor)
   D (Diffuser)
   A (Adhesion)
   N (Unspecified/None)

System Products:

The phenotypes observed through the visualization engine represent the prototype of a more faithful model of biological tissue. The visualization engine can continuously apply the ontogeny engine to provide fidelity to living (and thus continually developing) tissue.

There are two demonstrations of this fidelity: growth towards a stable form and maintenance of that form, such as repair upon injury.

Figure 14:
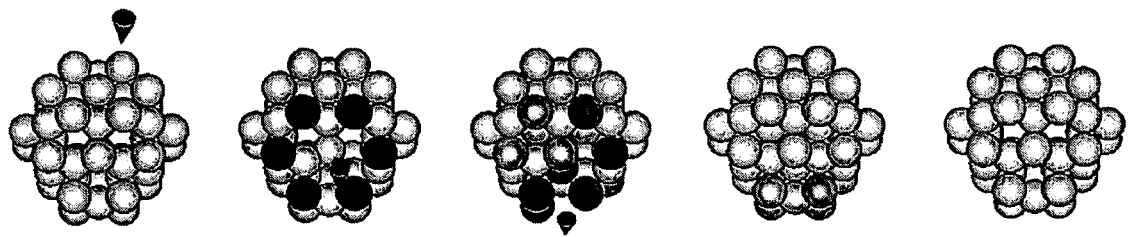
FIG. 14 is an illustration showing the Repair of a Hollow Sphere Shape.

In more complex shapes, shape maintenance and self-repair may be accomplished by more complex interactions between the cells, their neighbors, and the environment. FIG. 14 shows the self-repair of a hollow sphere. While this sequence may appear nearly identical to the repair of the solid cube in FIG. 9, the cells of the mature hollow sphere are light in color prior to injury, indicating inability to divide. Whereas in the solid cube individual, the restriction on growth is largely the result of cells having grown outside of the area of sufficient molecular concentration in the environment, the cells in the hollow sphere are held in a dynamic tension resulting from the mutual repression of each cell on its immediate neighbors. As long as a cell's neighbors are repressing it, it is unable to build up a sufficient concentration of growth molecule to divide. When injury occurs, however, cells adjacent to the removed cells become less repressed and are able to build up the required concentration of growth molecules to divide. As the injured area of the shape is filled, the new cells repress their parents, the parents likewise repress the new cells, and balance is restored.

Figure 15:
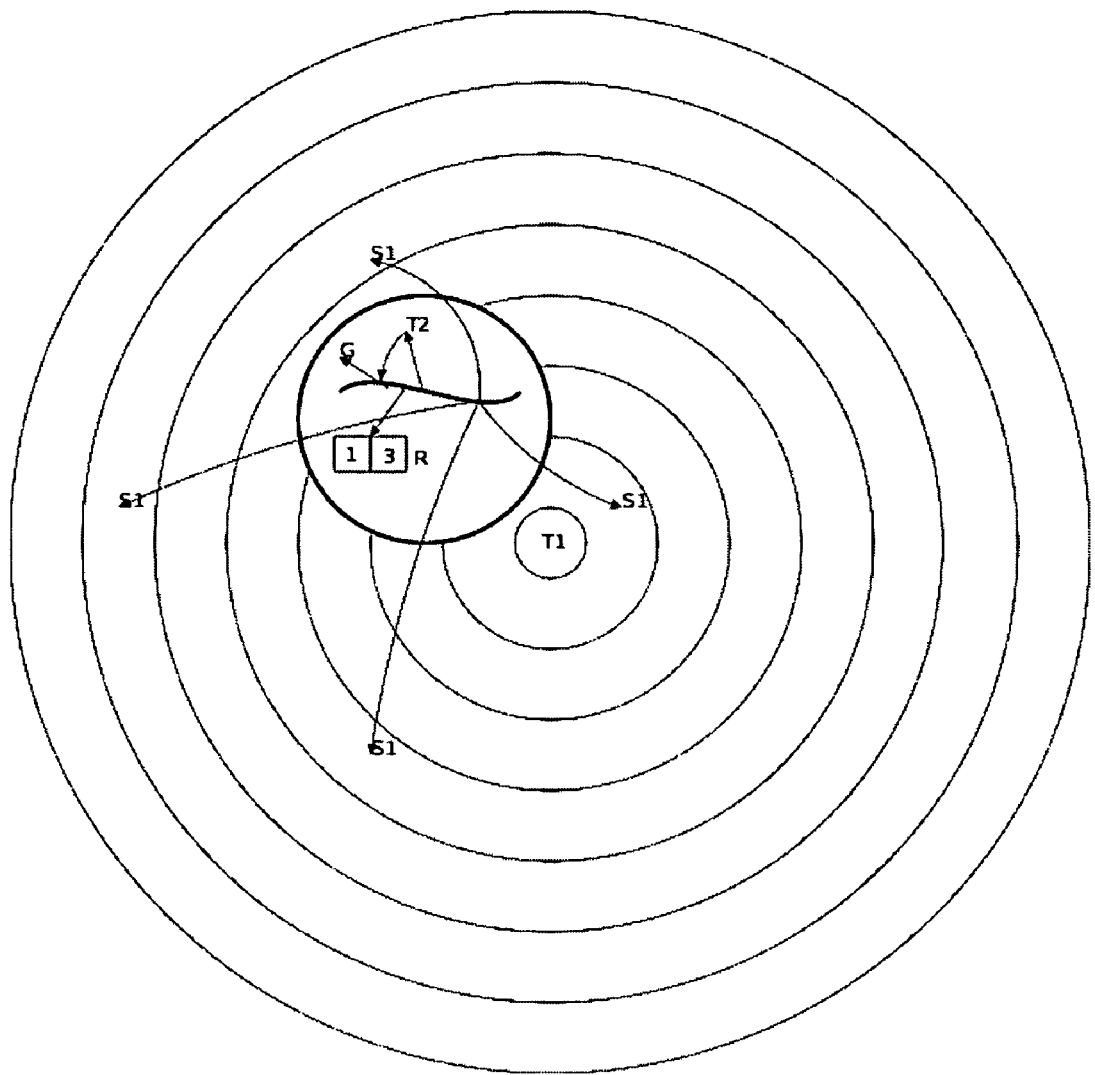
FIG. 15 is a diagram schematically illustrating the Starting Single Cell of a Hollow Sphere, showing the arrangement of a single cell being placed in the environment near a molecular source, resulting in the activation of four genes of the cell's genome.

What follows is a simplified, 2-dimensional illustration of the processes that produced such a hollow sphere shape, and allowed for self-repair. In FIG. 15, a single cell is placed in the environment near a molecular source placing T1 molecules in the environment such that the concentration of T1 molecules is highest at the source and decreases with increasing distance from the source. T1 molecules activate four genes of the cell's genome. The first activated gene produces growth molecule G. The second activated gene produces T2 molecules that repress the first gene, slowing production of G in subsequent steps. However, this self-repression is insufficient to prevent production of G due to the greater influence of T1. The third activated gene produces receptor molecules R in the cell that will produce T3 molecules when an S1 signal is received. The fourth activated gene produces a S1 signal molecules. Because the cell has no neighbors, its signals are not received by any other cells and, likewise, the cell's receptor molecules simply wait for the appropriate signal to be received.

Figure 16:
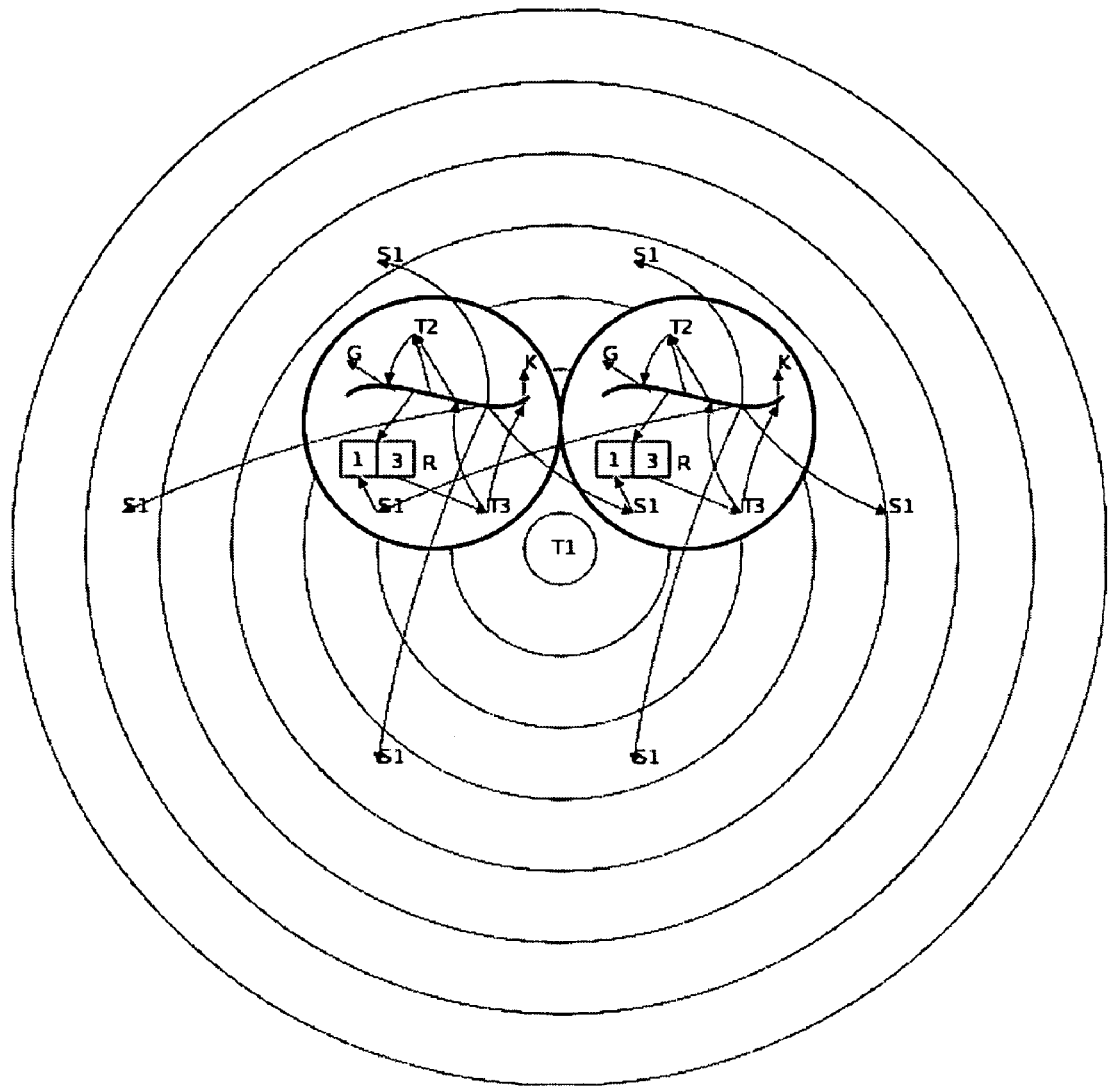
FIG. 16 is a diagram schematically illustrating Stage Two Division of the Hollow Sphere.

When sufficient G growth molecules have been accumulated in the original cell, it divides. As shown in FIG. 16, an illustration of stage two division of the hollow sphere, now that the cells each have a neighbor, they each signal each other with S1 molecules. The receptor molecules in each cell receive this signal and produce T3 molecules. The T3 molecules cause activation of two additional genes, and so on. One of those genes produces more T2 molecules, further slowing production of G, but insufficient to stop production of G due to the greater influence of T1. The second gene produces kill molecules K, but not in sufficient quantity to kill the cells.

Figure 17:
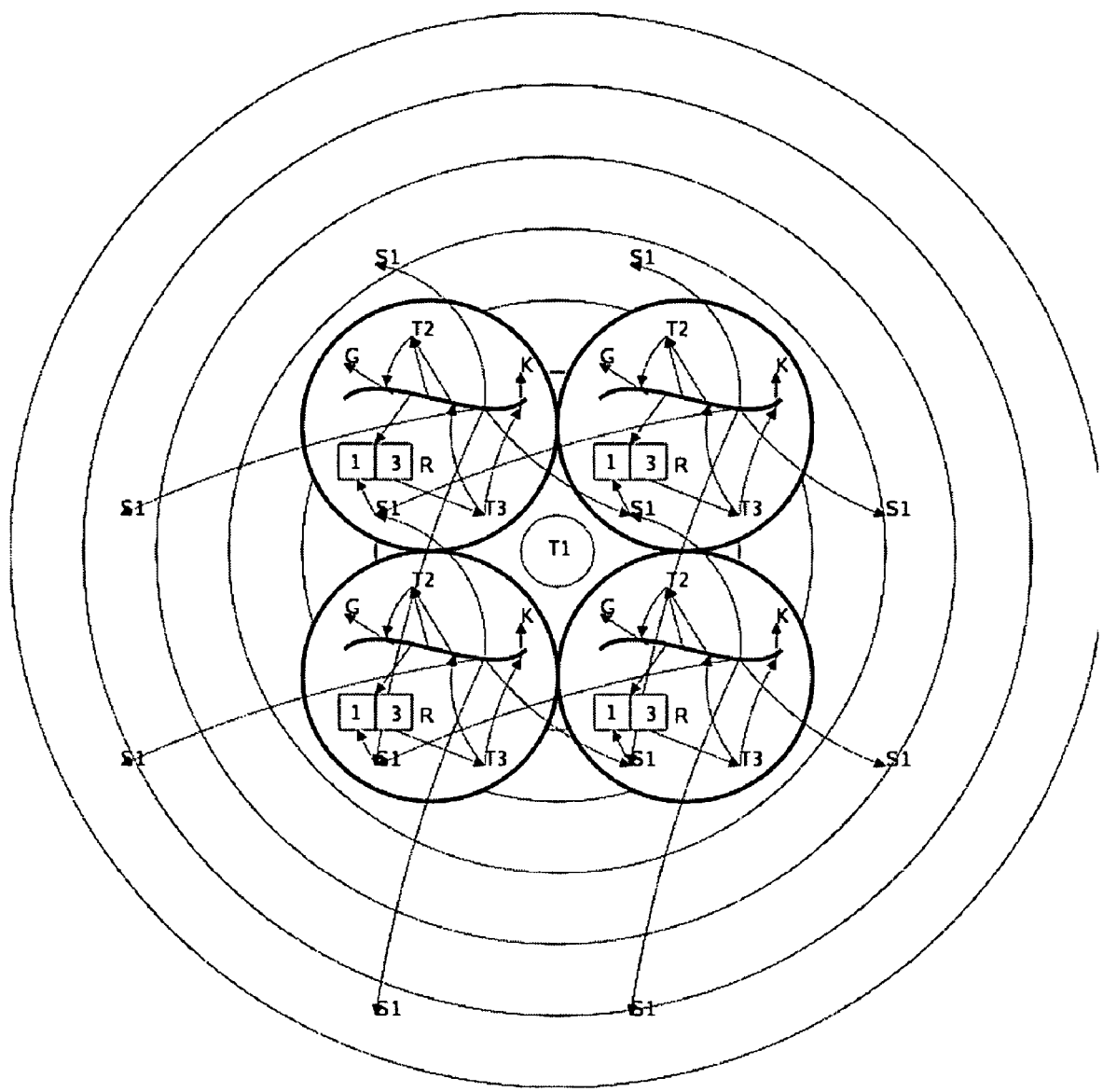
FIG. 17 is a diagram schematically illustrating Cells after Division Receiving Signals from Their Neighbors.
Figure 18:
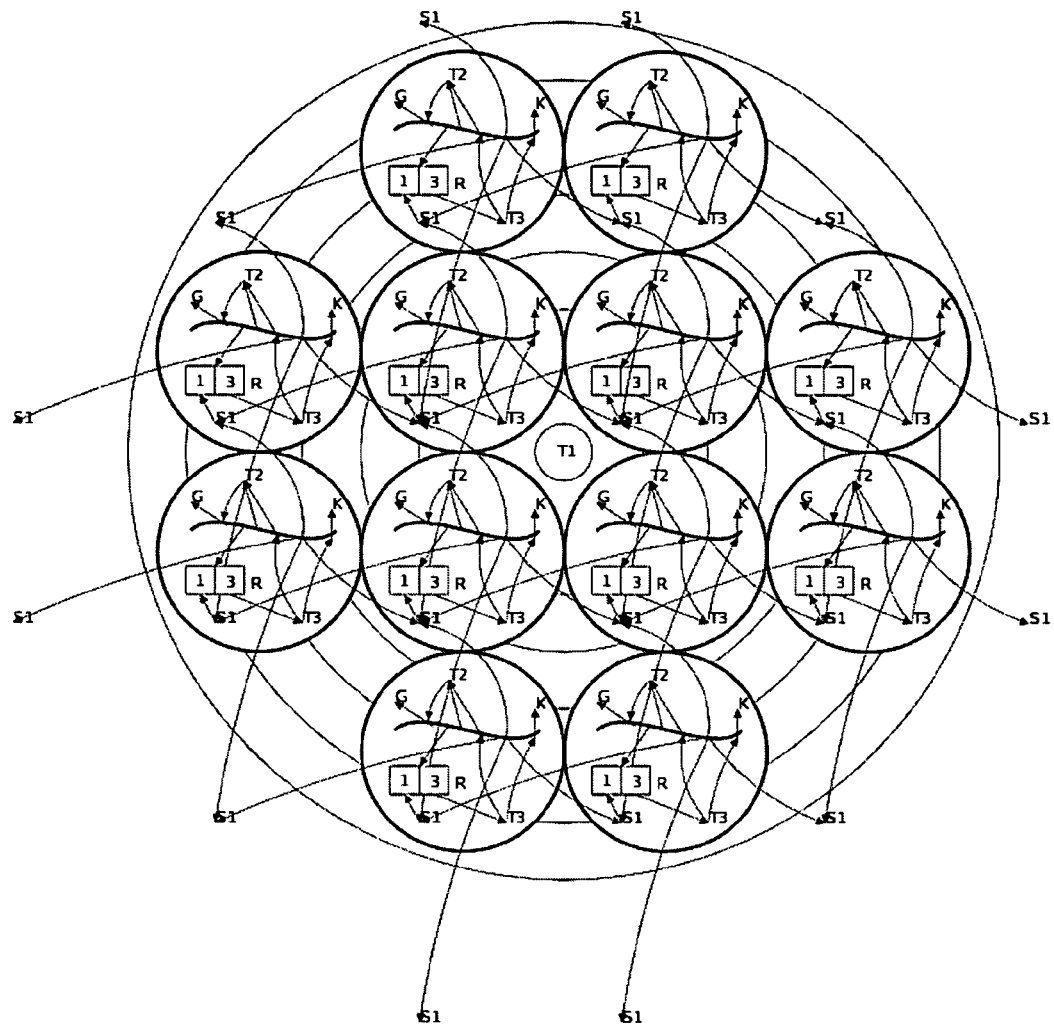
FIG. 18 is a diagram schematically illustrating Cell Division into the Interior of the Sphere.

After each of these cells divides, the embryo appears like FIG. 17. Each cell is signaling and receiving signals from two neighbors. Despite the mutual repression taking place, the influence of T1 is still enough to continue growth until the shape reaches a state like that in FIG. 18. Now that each interior cell is surrounded, it is receiving signals from four neighbors and is both sufficiently repressed to be unable to divide and is building up K molecules at a lethal rate. Exterior cells are far enough removed from the T1 source that the repression of a single neighbor is sufficient to prevent them from building up a sufficient concentration of G to divide.

Figure 19:
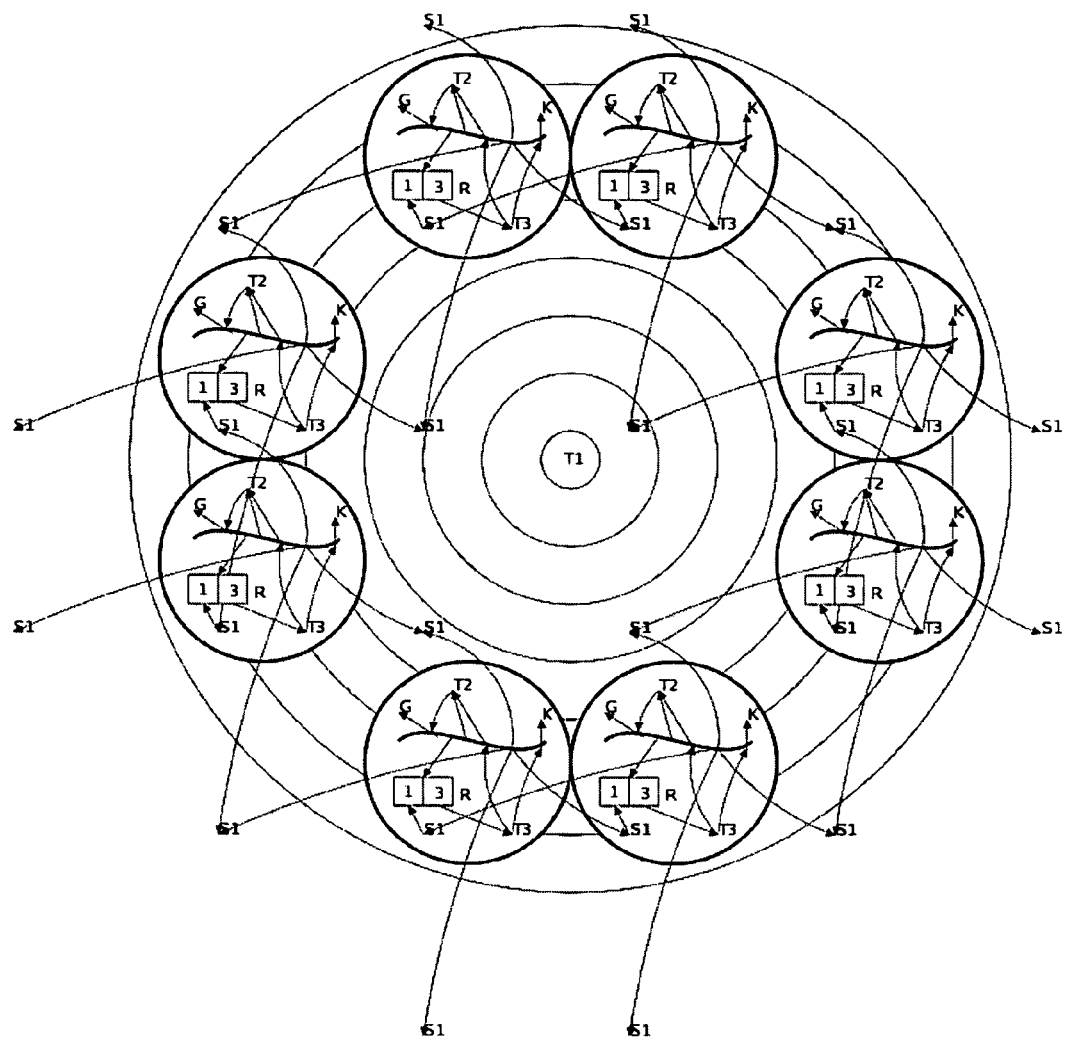
FIG. 19 is a diagram schematically illustrating Death of Interior Cells After Sufficient 'K' Molecule Concentration.

When the interior cells have built up a lethal concentration of K molecules, they die and the shape appears as a hollow sphere shape, as illustrated in FIG. 19. Despite removal of some neighbors, the exterior cells are still repressed from growing by having a single neighbor. Until some external actor perturbs this balance, all cells will remain in a state of dynamic tension.

Figure 20:
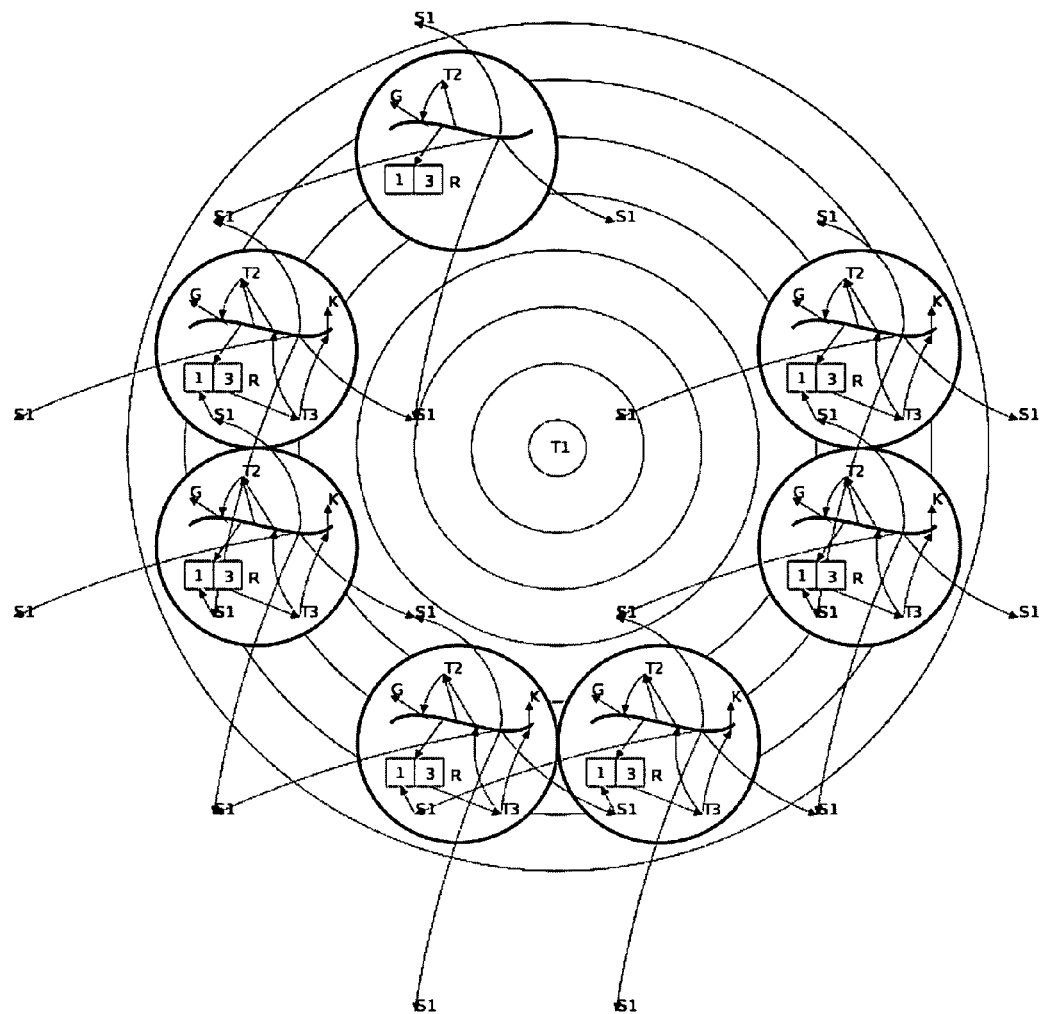
FIG. 20 is a diagram schematically illustrating Destruction and Repair of an External Cell in the Hollow Sphere.

If a cell is killed producing a shape like that in FIG. 20, it can be seen that the dead cell's neighbor becomes unrepressed and is capable of building up a sufficient concentration of G to divide once again. As in the self-repairing hollow sphere in FIG. 14, this injured shape would repair by first growing inward and filling out the shape from the inside, effectively returning to the state in FIG. 18 before returning to the state in FIG. 19.

Most of the above discussion is simply a narrative of the gene interactions that produced a different, but functionally equivalent, emergent behavior to the self-repair of the hollow cube. But this example could also be used to talk about how the present invention actually does model the Gene-to-Body concept (the one that showed the relationships between genotype, phenotype, and environment). Products of the genome (T2) feed back on the genome to change expression of other genes (G). Positioning in the environment and relative to other cells changes the rates of expression so that the interior cells require being surrounded before their growth is suppressed and before they build up a lethal concentration of K, while exterior cells can be repressed by a single neighbor and never build up lethal concentrations of K.

The hollow sphere being described is an evolved shape from a run seeded with a broken version of a similar hand-coded hollow sphere. The seed individual grows into a solid sphere close to the correct external target dimensions and exhibits self-repair, although not on par with the final individual. The evolved individual also self-repairs much better than the hand-coded individual that was used to generate the target and then broken to provide the search's seed individual. By "broken", it is meant that the effects of all genes in the hand-coded individual were leveled and so the evolution engine had to discover how to find the resulting evolved individual. The original individual was hand-coded using a different set of gradient builder equations than the final solution.

The following table, Table J, illustrates a Hand Designed Original Genome. The diagram illustrates a "hand" designed (i.e. human architect) genome which was intended to serve as both a learning process as well as an instance against which the machine evolved genome was to be compared.

TABLE J

Hand Designed Original Genome

```
<CsIndividual>
  <Version>0.3.8</Version>
  <Genome>
   [ [[1, 1] 6, [20, 1] -4] [[0, 0] G],
     [[1, 1] 3] [[20, 1] T],
     [[1, 1] 3] [[10, 1] S],
     [[1, 1] 7] [[10, 1, 15, 1] R],
     [[15, 1] 12] [[20, 1] T],
     [[15, 1] 10] [[0, 0] K] ]
  </Genome>
  <GradientBuilders> [ S [1, 1] @ 5 5 5 3 0.05 ] </GradientBuilders>
  <Environment>
    <CellGrid>
      <Dimensions>[11,11,11]</Dimensions>
      <CellPlacement>
        <AllAdjacent/>
        <Vacant/>
        <HighConcentration/>
      </CellPlacement>
      <CellSignal>
        <Local>
          <Neighborhood>
            <AllAdjacentNeighborhood/>
          </Neighborhood>
        </Local>
      </CellSignal>
      <Physics>
        <AffinityEvaluator>
          <DefaultAffinity/>
        </AffinityEvaluator>
        <PromotionEvaluator>
          <SmoothPromotion>
            <PromotionMidpoint>6</PromotionMidpoint>
            <ActiveConcentration>1</ActiveConcentration>
          </SmoothPromotion>
        </PromotionEvaluator>
      </Physics>
    </CellGrid>
  </Environment>
</CsIndividual>
```

The following table, Table K, depicts a Seed Individual Genome. The hollow sphere being described in the preceding drawings is an evolved shape from a run seeded with a "broken" version of a similar hand-coded hollow sphere. The evolved individual also self-repairs much better than the hand-coded individual that was used to generate the target and then broken to provide the search's seed individual. By "broken", it is meant that the effects of all genes in the hand-coded individual were leveled and so the evolution engine had to discover how to find the resulting evolved individual.

TABLE K

Seed Individual Genome

```
<CsIndividual>
  <Version>0.4.1</Version>
  <Genome>[
    [[1, 1] 4, [20, 1] -4] [[0, 0] G],
    [[1, 1] 4] [[20, 1] T],
    [[1, 1] 4] [[10, 1] S],
    [[1, 1] 4] [[10, 1, 15, 1] R],
    [[15, 1] 4] [[20, 1] T],
    [[15, 1] 4] [[0, 0] K]
  ]</Genome>
```

TABLE K-continued

Seed Individual Genome

```
  <GradientBuilders><UseModifier/>
    [ S [1, 1] @ 5 5 5 3 0.05 1 ]
  </GradientBuilders>
  <Environment>
    <CellGrid>
      <Dimensions>[11,11,11]</Dimensions>
      <CellPlacement>
        <AllAdjacent/>
        <Vacant/>
        <HighConcentration/>
      </CellPlacement>
      <CellSignal>
        <Local>
          <Neighborhood>
            <AllAdjacentNeighborhood/>
          </Neighborhood>
        </Local>
      </CellSignal>
      <Physics>
        <AffinityEvaluator>
          <DefaultAffinity/>
        </AffinityEvaluator>
        <PromotionEvaluator>
          <SmoothPromotion>
            <PromotionMidpoint>6</PromotionMidpoint>
            <ActiveConcentration>1</ActiveConcentration>
          </SmoothPromotion>
        </PromotionEvaluator>
      </Physics>
    </CellGrid>
  </Environment>
</CsIndividual>
```

The following table, Table L, shows an Evolved Genome for a Self-Healing Hollow Sphere. The table shows the resulting genome as it was evolved using the Evolution Engine. The resulting phenotype (hollow sphere) demonstrated superior self-repair characteristics than the phenotype resulting from the hand-designed genome.

TABLE L

Evolved Genome for a Self-Healing Hollow Sphere

```
<CsIndividual>
  <Version>0.4.1</Version>
  <Genome>[
    [[1, 0.808101236820221] 6.52933979034424,
    [20, 0.541983604431152] - 5.88963937759399]
    [[0, 0.550654768943787] G],
    [[1, 0.777882993221283] 3.94237232208252]
  [[20, 0.770480096340179] T],
    [[1, 1.05560564994812] 5.80799436569214]
  [[10, 0.843806028366089] S],
    [[1, 1.07641875743866] 7.32759141921997]
    [[10, 1.39490437507629, 15, 1] R],
    [[15, 0.514424026012421] 7.28170824050903]
  [[20, 1.44415986537933] T],
    [[15, 1.83406269550323] 5.87176609039307]
  [[0, 0.700968086719513] K]
  ]</Genome>
  <GradientBuilders><UseModifier/>
    [S [1, 0.978522002696991]
       @ 5 5 5 3.35959887504578 0.106650061905384 1]
  </GradientBuilders>
  <Environment>
    <CellGrid>
      <Dimensions>[11,11,11]</Dimensions>
      <CellPlacement>
        <AllAdjacent/>
        <Vacant/>
        <HighConcentration/>
      </CellPlacement>
```

TABLE L-continued

Evolved Genome for a Self-Healing Hollow Sphere

```
        <CellSignal>
            <Local>
                <Neighborhood>
                    <AllAdjacentNeighborhood/>
                </Neighborhood>
            </Local>
        </CellSignal>
        <Physics>
            <AffinityEvaluator>
                <DefaultAffinity/>
            </AffinityEvaluator>
            <PromotionEvaluator>
                <SmoothPromotion>
                    <PromotionMidpoint>6</PromotionMidpoint>
                    <ActiveConcentration>1</ActiveConcentration>
                </SmoothPromotion>
            </PromotionEvaluator>
        </Physics>
        </CellGrid>
    </Environment>
</CsIndividual>
```

What is claimed is:

1. A method in a suitably programmed computer system for modeling virtual biological tissue, the method comprising:

receiving modeling information by the suitably programmed computer system, wherein the modeling information includes one or more virtual environmental parameters and one or more virtual genes, and wherein the one or more virtual genes define one or more distinct virtual genomes;

in response to the modeling information, generating a virtual environment based on the environmental parameters, and generating one or more virtual cells in the virtual environment, the one or more virtual cells each comprising an individual distinct virtual genome, wherein the individual distinct virtual genome is configured to interact with the virtual environment, and wherein the individual distinct virtual genome and the environmental parameters are configured to be modified by genetic operations;

running an ontogeny engine to develop multicellular individuals from the one or more virtual cells, according to biological primitives specified by each of the distinct virtual genomes, during exposure to the virtual environment;

evaluating and selecting one or more of the multicellular individuals according to a fitness criterion;

modifying at least one of the distinct virtual genomes of the selected multicellular individuals and one or more virtual environmental parameters;

running the ontogeny engine to develop a next generation of multicellular individuals; and evaluating a behavior of each of the next generation of multicellular individuals and identifying next generation multicellular individuals that exhibit adaptive emergent functionality in response to a stimulus.

2. The method of claim 1, wherein the one or more virtual environmental parameters are rules governing one or more virtual factors selected from the group consisting of placement of nutrients, concentration of nutrients, space for growth, sequencing of biological actions, molecular affinity, and physics of environment.

3. The method of claim 1, wherein the biological primitives are one or more virtual functions selected from the group consisting of self-construction, growth, self-replication, compartmentalization, specialization, feedback, communication, metabolism, and death.

4. The method of claim 1, wherein the genetic operations are one or more selected from the group consisting of mutation, duplication, deletion, or cross-over.

5. The method of claim 1, wherein the fitness criterion comprises a stable or homeostatic shape of a multicellular individual that matches a target shape.

6. The method of claim 1, wherein the adaptive emergent functionality comprises self-repair.

7. The method of claim 1, wherein the stimulus comprises a perturbation to a multicellular individual provided by user interaction.

8. A suitably programmed computer system having a processor and memory for modeling virtual biological tissue, comprising:

a first means for
receiving modeling information, wherein the modeling information includes one or more virtual environmental parameters and one or more virtual genes, and wherein the one or more virtual genes define one or more distinct virtual genomes;

generating a virtual environment based on the environmental parameters, and generating one or more virtual cells in the virtual environment, the one or more virtual cells each comprising an individual distinct virtual genome, wherein the individual distinct virtual genome is configured to interact with the virtual environment, and wherein the individual distinct virtual genome and the environmental parameters are configured to be modified by genetic operations; and developing multicellular individuals from the one or more virtual cells, according to biological primitives specified by each distinct virtual genome, during exposure to the virtual environment;

a second means for
evaluating and selecting multicellular individuals according to fitness criteria; and modifying at least one of the distinct virtual genomes of the selected multicellular individuals and one or more virtual environmental parameters to develop a next generation of the multicellular individuals; and a third means for evaluating a behavior of each of the next generation of multicellular individuals and identifying next generation multicellular individuals that exhibit adaptive emergent functionality in response to a stimulus;

wherein the first, second and third means are implemented as instructions stored in the memory for execution by the processor.

9. The system of claim 8, wherein the one or more environmental parameters are rules governing one or more virtual factors selected from the group consisting of placement of nutrients, concentration of nutrients, space for growth, sequencing of biological actions, molecular affinity, and physics of environment.

10. The system of claim 8, wherein the biological primitives are one or more virtual functions selected from the group consisting of self-construction, growth, self-replication, compartmentalization, specialization, feedback, communication, metabolism, and death.

11. The system of claim 8, wherein the genetic operations are one or more selected from the group consisting of mutation, duplication, deletion, or cross-over.

12. The system of claim 8, wherein the fitness criterion comprises a stable or homeostatic shape of a multicellular individual that matches a target shape.

13. The system of claim 8, wherein the adaptive emergent functionality comprises self-repair.

14. The system of claim 8, wherein the stimulus comprises a perturbation to a multicellular individual provided by user interaction.

15. An apparatus for modeling virtual biological tissue, the apparatus comprising:
- a processor;
- a memory for data and programming instruction storage;
- programming instructions stored in the memory for execution by the processor, wherein the programming instructions, if executed by the processor, cause the processor to
  - generate a virtual environment and a population of virtual cells, the virtual cells each comprising a configurable virtual genome, wherein the configurable virtual genome is configured to interact with the virtual environment, and wherein the configurable virtual genome and the virtual environment are configured to be modified by genetic operations;
  - run an ontogeny engine to develop multicellular individuals from individual virtual cells in the population of virtual cells according to biological primitives specified by each configurable virtual genome during exposure to the virtual environment;
  - run an evolutionary engine to conduct an evolutionary search, wherein the evolutionary search includes evaluating and selecting multicellular individuals according to fitness criteria;
  - run the evolutionary engine to modify at least one of the configurable virtual genomes of one or more of the selected multicellular individuals and the virtual environment;
  - run the ontogeny engine to develop a next generation of multicellular individuals; and
  - evaluate a behavior of each of the next generation of multicellular individuals and identify next generation multicellular individuals that exhibit adaptive emergent functionality in response to a stimulus; and
- an output device for communicating data relating to the identified next generation multicellular individuals.

16. The apparatus of claim 15, wherein the virtual environment is generated based on rules governing one or more virtual factors selected from the group consisting of placement of nutrients, concentration of nutrients, space for growth, sequencing of biological actions, molecular affinity, and physics of environment.

17. The apparatus of claim 15, wherein the biological primitives are one or more virtual functions selected from the group consisting of self-construction, growth, self-replication, compartmentalization, specialization, feedback, communication, metabolism, and death.

18. The apparatus of claim 15, wherein the genetic operations are one or more selected from the group consisting of mutation, duplication, deletion, or cross-over.

19. The apparatus of claim 15, wherein the fitness criterion comprises a stable or homeostatic shape of a multicelluar individual that matches a target shape.

20. The apparatus of claim 15, wherein the adaptive emergent functionality comprises self-repair.

21. The apparatus of claim 15, wherein the stimulus comprises a perturbation to a multicellular individual provided by user interaction.

* * * * *